United States Patent
Kuroda et al.

(10) Patent No.: US 7,632,411 B2
(45) Date of Patent: Dec. 15, 2009

(54) METHOD FOR DETECTING FILTER CLOGGING BY USING PRESSURE INFORMATION, APPARATUS FOR MONITORING FILTER CLOGGING AND BED-SIDE SYSTEM

(75) Inventors: Yasuhiro Kuroda, Tokushima (JP);
Yohsuke Kinouchi, Tokushima (JP);
Masatake Akutagawa, Tokushima (JP);
Toshiya Okahisa, Tokushima (JP);
Yoshiaki Ohnishi, Tokushima (JP)

(73) Assignee: Koninklijke Philips Electronics N.V., Eindhoven (NL)

( * ) Notice: Subject to any disclaimer, the term of this patent is extended or adjusted under 35 U.S.C. 154(b) by 862 days.

(21) Appl. No.: 10/545,990

(22) PCT Filed: Feb. 11, 2004

(86) PCT No.: PCT/IB2004/000415

§ 371 (c)(1),
(2), (4) Date: Aug. 18, 2005

(87) PCT Pub. No.: WO2004/073772

PCT Pub. Date: Sep. 2, 2004

(65) Prior Publication Data

US 2006/0157408 A1    Jul. 20, 2006

(30) Foreign Application Priority Data

Feb. 19, 2003    (JP)    ............... 2003-041731

(51) Int. Cl.
*B01D 11/00* (2006.01)
*B01D 21/24* (2006.01)
*B01D 24/38* (2006.01)
*C02F 1/44* (2006.01)

(52) U.S. Cl. ............. 210/645; 210/321.71; 210/321.69; 210/90; 210/97; 210/103; 210/644; 210/321.8

(58) Field of Classification Search ................. 210/645, 210/321.69, 321.71, 321.8, 90, 97, 103, 106, 210/650, 644
See application file for complete search history.

(56) References Cited

U.S. PATENT DOCUMENTS 5,069,792 A * 12/1991 Prince et al. ................. 210/637

(Continued)

FOREIGN PATENT DOCUMENTS

| EP | 0 330 761 A1 | 9/1989 |
| EP | 0 611 228 A2 | 8/1994 |
| JP | 8-33706 A | 2/1996 |
| JP | 11-104233 A | 4/1999 |
| WO | WO 2004/002553 A1 | 1/2004 |

OTHER PUBLICATIONS

Author Unknown; J. of Japanese Soc. for Dialysis Therapy, vol. 35, p. 616, Jun. 20, 2002. (as listed in the specification).

Primary Examiner—Ana M Fortuna

(57) ABSTRACT

A method is provided for detecting filter clogging which are able to keep track of the filter clogging with precision and in detail. At least one pressure selected from the group consisting of a pressure Pa in a blood inflow portion (32a), a pressure Pv in a blood outflow portion (32b), a pressure Pf1 in a filtrate inflow portion (32c), and a pressure Pf2 in a filtrate outflow portion (32d) is measured continuously, then a variation (pressure waveform) of the pressure is analyzed, a clogging of a filter (32) is detected using the analyzed result. Thereby a clogging of a filter is detected early. As a result, it is possible to prevent from developing of the filter clogging by controlling a dosage amount of anti-coagulant properly and changing a flow rate of blood. The variation of the pressure wave may be analyzed by subjecting the variable to Fast Fourier Transform.

13 Claims, 18 Drawing Sheets

U.S. PATENT DOCUMENTS

| | | | | |
|---|---|---|---|---|
| 5,368,555 A | * | 11/1994 | Sussman et al. | 604/6.05 |
| 5,595,138 A | * | 1/1997 | Claret | 116/268 |
| 5,690,831 A | * | 11/1997 | Kenley et al. | 210/646 |
| 5,702,597 A | * | 12/1997 | Chevallet et al. | 210/195.2 |
| 5,716,531 A | * | 2/1998 | Kenley et al. | 210/746 |
| 5,863,421 A | * | 1/1999 | Peter et al. | 210/134 |
| 7,254,518 B2 | * | 8/2007 | Eryurek et al. | 702/183 |
| 7,478,010 B2 | * | 1/2009 | Hashemian | 702/151 |
| 2002/0099286 A1 | | 7/2002 | Sandler et al. | |
| 2002/0174721 A1 | | 11/2002 | Gross | |

* cited by examiner (a) A point (b)

(a)

(b)

(a) V Chamber Forward Return Model (b) Tank Return Model

METHOD FOR DETECTING FILTER CLOGGING BY USING PRESSURE INFORMATION, APPARATUS FOR MONITORING FILTER CLOGGING AND BED-SIDE SYSTEM

BACKGROUND OF THE INVENTION

1. Field of the Invention

The present invention relates to a method for detecting filter clogging, an apparatus for monitoring filter clogging and bed-side system, more particularly the present invention relates to a method for detecting filter clogging used in a blood purifying system, an apparatus for monitoring filter clogging on the basis of the filter clogging, and a bed-side system having the apparatus.

2. Description of Related Art

A blood purification method is roughly classified into two types. One is a type that removes substances in the blood through transfer (diffusion or filtering) to a waste liquid or adsorption into a membrane when the blood flows in a hollow-fiber of a filter, and hemodialysis, hemofiltering, hemodiafiltering, plasma exchange, double filtering plasmapheresis, plasmapheresis are some examples of this type. The other is a type that removes substances in the blood through adsorption into an adsorbent in a filter when the blood passes through the adsorbent (cloth, bead, etc.), and blood adsorption is an example of this type.

The former type of blood purification method requires a filter for dialyzing or filtering the blood. The clogging of the filter is prevented from occurring by using an anti-coagulant or adjusting a flow rate at medical sites.

As a method of optimizing a filter flow rate using filter pressure information, for example, Patent Document 1 discloses a control system using the trans-membrane pressure (TMP). Patent Document 2 discloses a dialysis therapy apparatus provided with a device for monitoring removal of an injection needle which serves as an inlet and outlet of the blood, by monitoring pressure information, particularly, pressure pulsing information in a dialyzing fluid path.

Further, Non-Patent Document 1 discloses a method of calculating an internal filtering flow rate using a result of Fast Fourier Transform of the pressure in frequency analysis to monitor the filtering efficiency in filtering dialysis using a membrane with high water permeability (JP05-508584, JP11-104233, and Journal of Japanese Society for Dialysis Therapy, Vol. 35, The Japanese Society for Dialysis Therapy, page 616 "WS14-6", Jun. 20, 2002).

However, overdosage of an anti-coagulant in an attempt to prevent clogging of a filter may cause a danger of producing serious hemorrhagic complications (cerebral hemorrhage, etc.).

Further, there is an economical problem because the anti-coagulant is expensive.

Therefore, it is desirable to detect the clogging of a filter early, adjust a dosage amount of the anti-coagulant properly and control the flow rate to prevent the clogging from developing.

In view of the foregoing, it is an object of the present invention to provide a method for detecting filter clogging, an apparatus for monitoring filter clogging on the basis of the filter clogging and bed-side system having the apparatus which are able to keep track of the filter clogging with precision and in detail.

SUMMARY OF THE INVENTION

The inventors of the present invention thought that in order to keep track of the filter clogging with precision and in detail, using filter pressure information enables keeping track of the filter clogging to be carried out with precision and in detail, reached the invention, and applied for a patent on the invention (Japanese Patent Application No. 2002-187949).

FIG. 1a is a view schematically showing a function of a roller pump as an example of liquid feeding means. The blood purification apparatus feeds a liquid such as blood and filtrate using a roller pump that pushes a tube 404 of the circuit by a rotor 402 as shown FIG. 1(a). Therefore, the circuit internal pressure exhibits a pulsing waveform as shown in FIG. 1(b). By setting the number of rotations of the rotor 402, it is possible to flow a constant amount of liquid in a constant time, and the frequency of the circuit internal pressure wave is determined by the number of times the rotor 402 pushes the tube. The filter clogging is a state where substances such as protein and blood cell in the blood adhere to the internal surface and side holes of a hollow-fiber of the filter, a narrowing thereby occurs in a flow path of liquid such as the blood and filtrate, and the liquid is hard to flow.

FIG. 2 is a view showing a shift of the pressure waveform due to a narrowing of a flow path. FIG. 2(a) shows a pressure waveform without the narrowing, FIG. 2(b) shows a pressure waveform with the narrowing of light to medium degree, and FIG. 2(c) shows a pressure waveform with the narrowing of strong degree. The inventors of the present invention noted that when the narrowing occurs in the flow path (filer or circuit) 202 of the liquid by the roller pump, variations in degree of narrowing not only increase the means of the circuit internal pressure, but also varies a waveform (amplitude, etc.) of the pressure waveform of the circuit internal pressure, as shown in FIG. 2(a) to 2(c), thought whether measuring variations in waveform component of the pulsing wave of the circuit internal pressure in a single measuring portion enables evaluation of the degree of filter clogging, and studied such a method.

Further, as can be seen from that respective pressure waveforms of A point and B point in the flow path 202 of the liquid as shown in FIG. 3(a) are different from each other as shown in FIG. 3(b), a decrease in amplitude and phase shift occur in the waveform corresponding to the state of the flow path as the pressure waves propagate. The inventors of the present invention noted this respect, and studied whether it is possible to detect effective information with respect to the filter clogging, by measuring variations in amplitude and phase difference in two measurement portions to check the ease of propagation of the pressure wave. As a result, the inventors of the present invention found out that it is possible to recognize the status of the filter clogging by analyzing the waveform of the pressure wave inside the circuit, and reached the present invention.

Namely, it is a gist of the present invention continuously measuring at least one pressure of a pressure in a blood inflow portion, a pressure in a blood outflow portion, a pressure in a filtrate inflow portion, and a pressure in a filtrate outflow portion, analyzing a variation (in pressure waveform) with time, and detecting filter clogging using the analyzed result. Thereby a filter clogging is detected early. It is thus possible to prevent the filter clogging from developing by controlling a dose amount of anti-coagulant properly and changing a flow rate of blood.

According to a first aspect of the present invention, a method for detecting filter clogging according to the present invention is a method for detecting a filter clogging composed of hollow-fiber membrane, which has a blood inflow portion, a blood outflow portion, a filtrate inflow portion, and a filtrate outflow portion, and which filters a blood by passing the blood, and has the steps of 1) continuous measuring at least one pressure selected from the group consisting of a pressure in the blood inflow portion, a pressure in the blood outflow portion, a pressure in the filtrate inflow portion, and a pressure in the filtrate outflow portion, 2) analyzing a variation of the measured pressure in the measuring step, and 3) detecting a filter clogging using an analyzed result in the analyzing step.

Herein, it is preferable that a transformed value is calculated by subjecting the variation to Fast Fourier Transform in the analyzing step.

Herein, it is preferable that a filter clogging is detected using a transformed value corresponding to pulsing frequency in at least one of the blood inflow portion and the filtrate outflow portion in the detecting step.

Herein, it is preferable that a filter clogging is detected using amplitude and/or power of the transformed value in the detecting step.

Herein, it is preferable that a filter clogging is detected using a ratio of amplitude and/or power in at least two of the blood inflow portion, the blood outflow portion, the filtrate inflow portion, and the filtrate outflow portion in the detecting step.

Herein, it is preferable that a filter clogging is detected using a phase of the transformed value in the detecting step.

Herein, it is preferable that a filter clogging is detected using a difference of phase in at least two of the blood inflow portion, the blood outflow portion, the filtrate inflow portion, and the filtrate outflow portion in the detecting step.

According to a second aspect of the present invention, an apparatus for monitoring a filter clogging according to the present invention has detecting means for detecting a filter clogging by the method for detecting a filter clogging as described above, displaying means for displaying the filter clogging on the basis of a detected result of the detecting means, and monitoring means for monitoring the filter clogging on the basis of the detected result of the detecting means.

According to a third aspect of the present invention, a bed-side system according to the present invention has the apparatus for monitoring a filter clogging as described above.

BRIEF DESCRIPTION OF THE DRAWINGS

FIG. 1a is a view schematically showing a function of a roller pump; FIG. 1b is a view showing a pressure waveform in A point of FIG. 1a;

FIG. 3a is a view schematically showing a measuring point of the pressure waveform, FIG. 3b is a view showing pressure waveforms in A point and B point of FIG. 3a;

DESCRIPTION OF THE PREFERRED EMBODIMENT(S)

Embodiments of the present invention will be described specifically below with reference to accompanying drawings.

Figure 1:
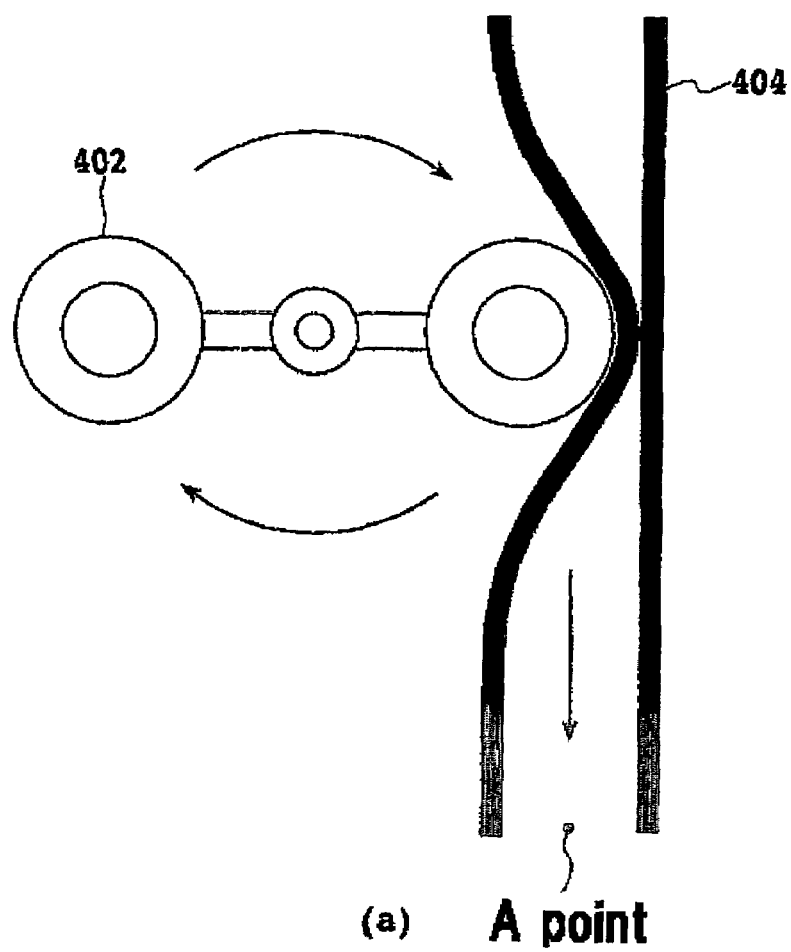
Figure 1:
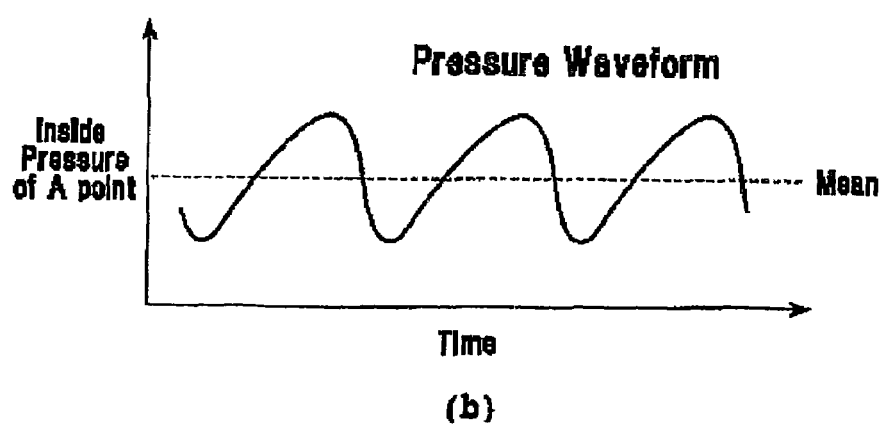
Figure 2:
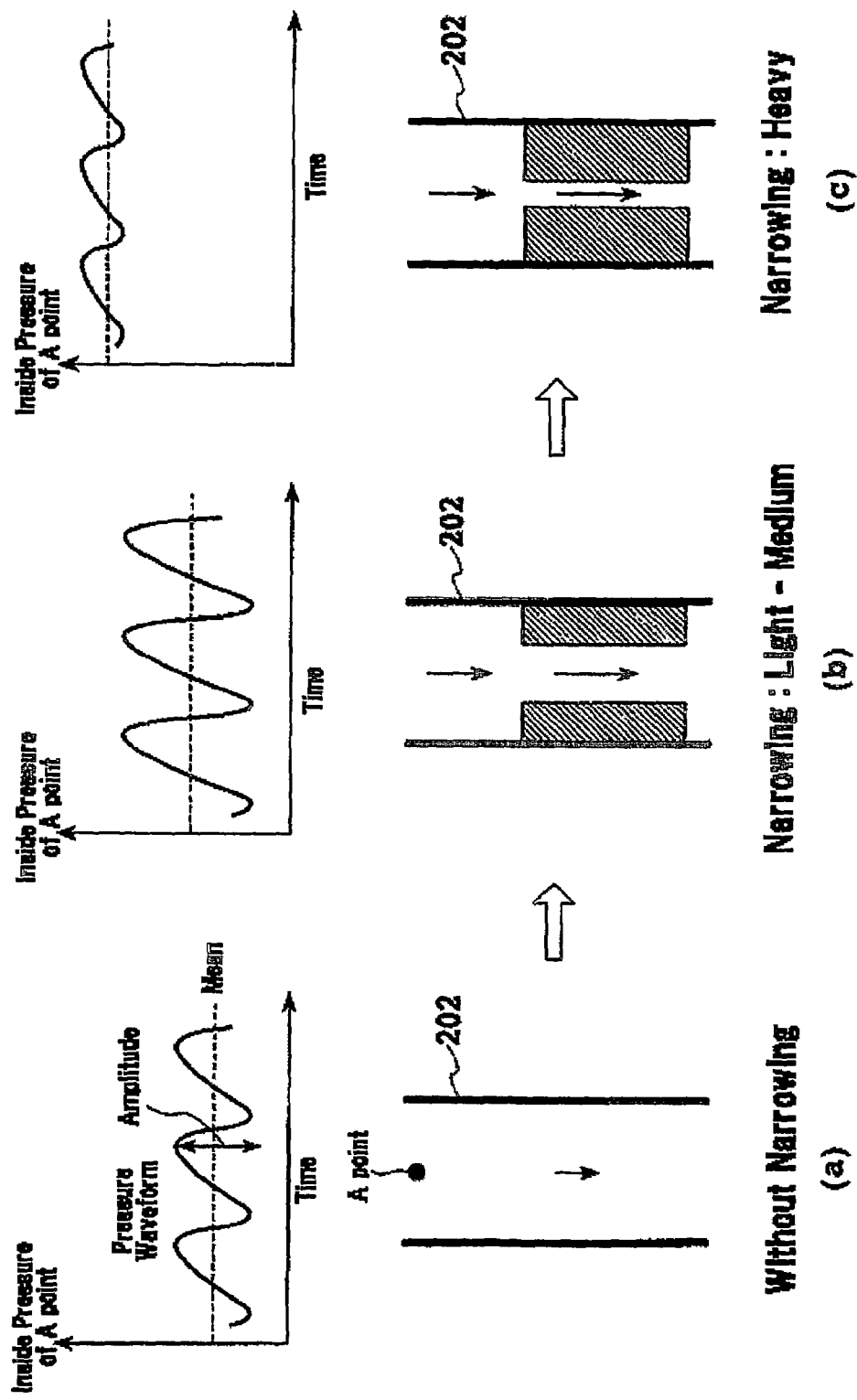
FIG. 2 is a view showing a shift of the pressure waveform due to a narrowing of a flow path.
Figure 3:
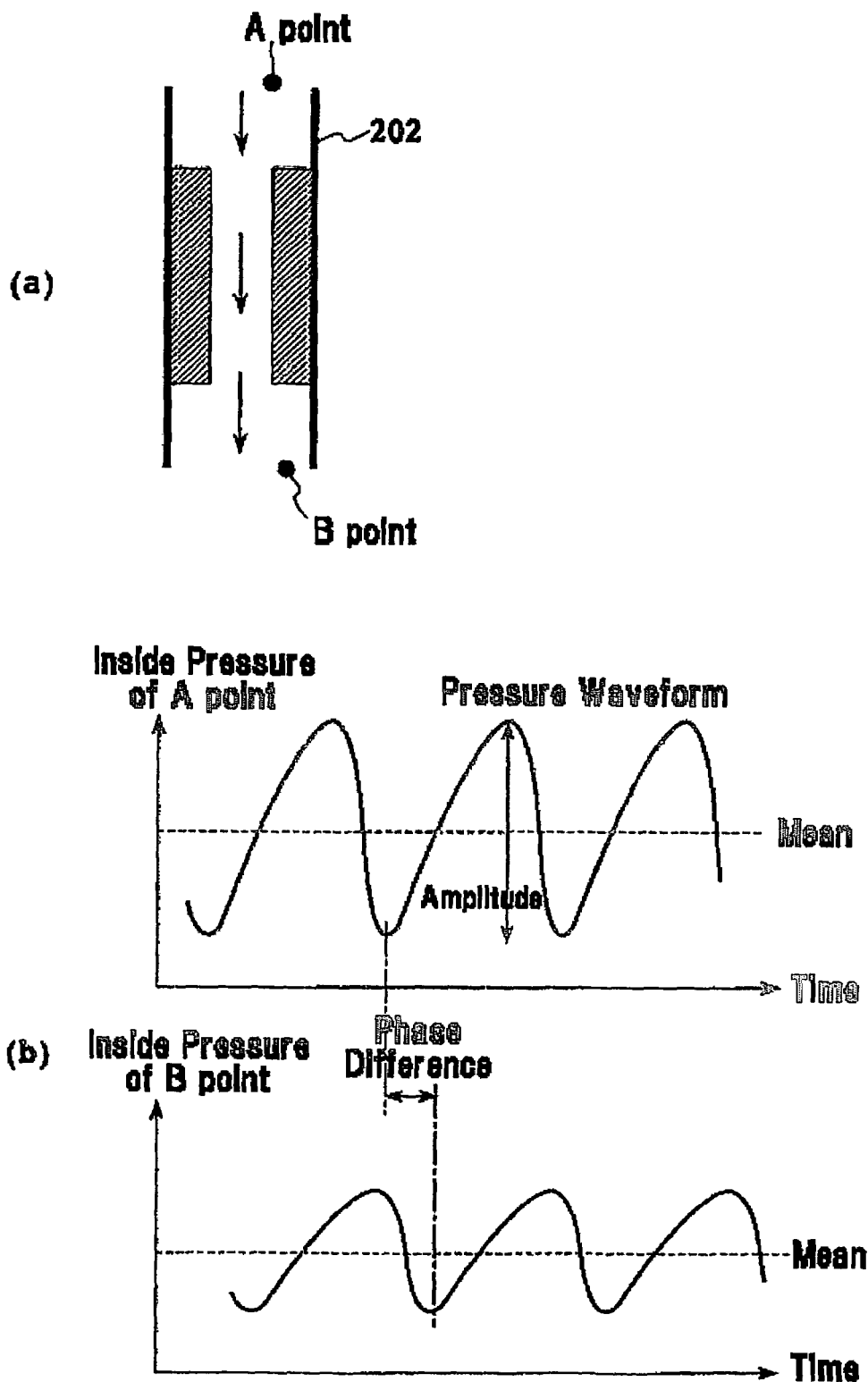
FIGS. 3a and 3b are views showing a shift of the pressure waveform.
Figure 4:
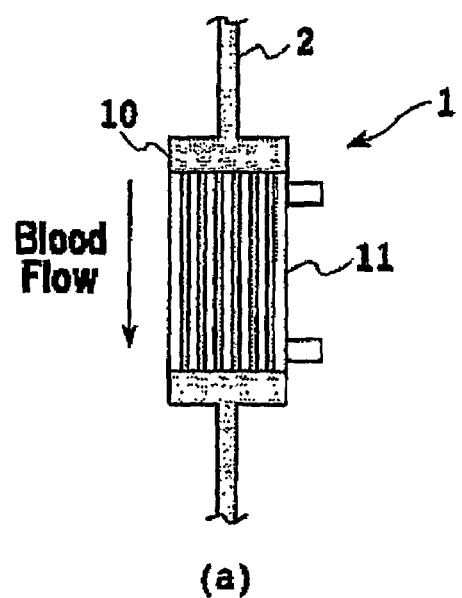
FIG. 4a is a view schematically showing a filter for purifying blood.
FIG. 4b is a view schematically showing hollow-fiber membrane of the filter.
Figure 4:
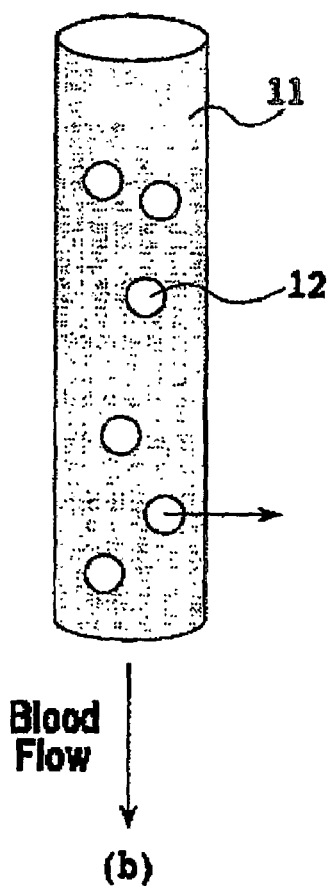

First, a filter clogging mode will be described with reference to FIG. 4. A filter 1 for use in blood purification is composed of several thousand to ten and several thousand hollow-fibers 11 disposed in a housing 10 as shown in FIG. 4(a), and each of the hollow-fibers 11 has an effective length of approximately 150 to 250 mm and an inside diameter of approximately 200 μm in a humid condition. The filter 1 is connected to a circulation path 2 for circulating the bodily fluid such as blood. Further as shown in FIG. 4(b), many fine holes 12 each with a diameter of several ten angstroms are formed on the side of the hollow-fiber 11. Clogging in such a hollow-fiber during blood purification can be roughly classified into two types of clogging; clogging in the direction of blood flow due to clogging inside the hollow-fiber (clogging indicating the reduction in flowing ease of the blood: vertical clogging) and clogging in the direction of from the blood to filtrate (or dialyzing fluid) due to clogging of a fine hole of the hollow-fiber membrane (clogging indicating the reduction in removal capability to a waste liquid in filtering: lateral clogging).

Figure 5:
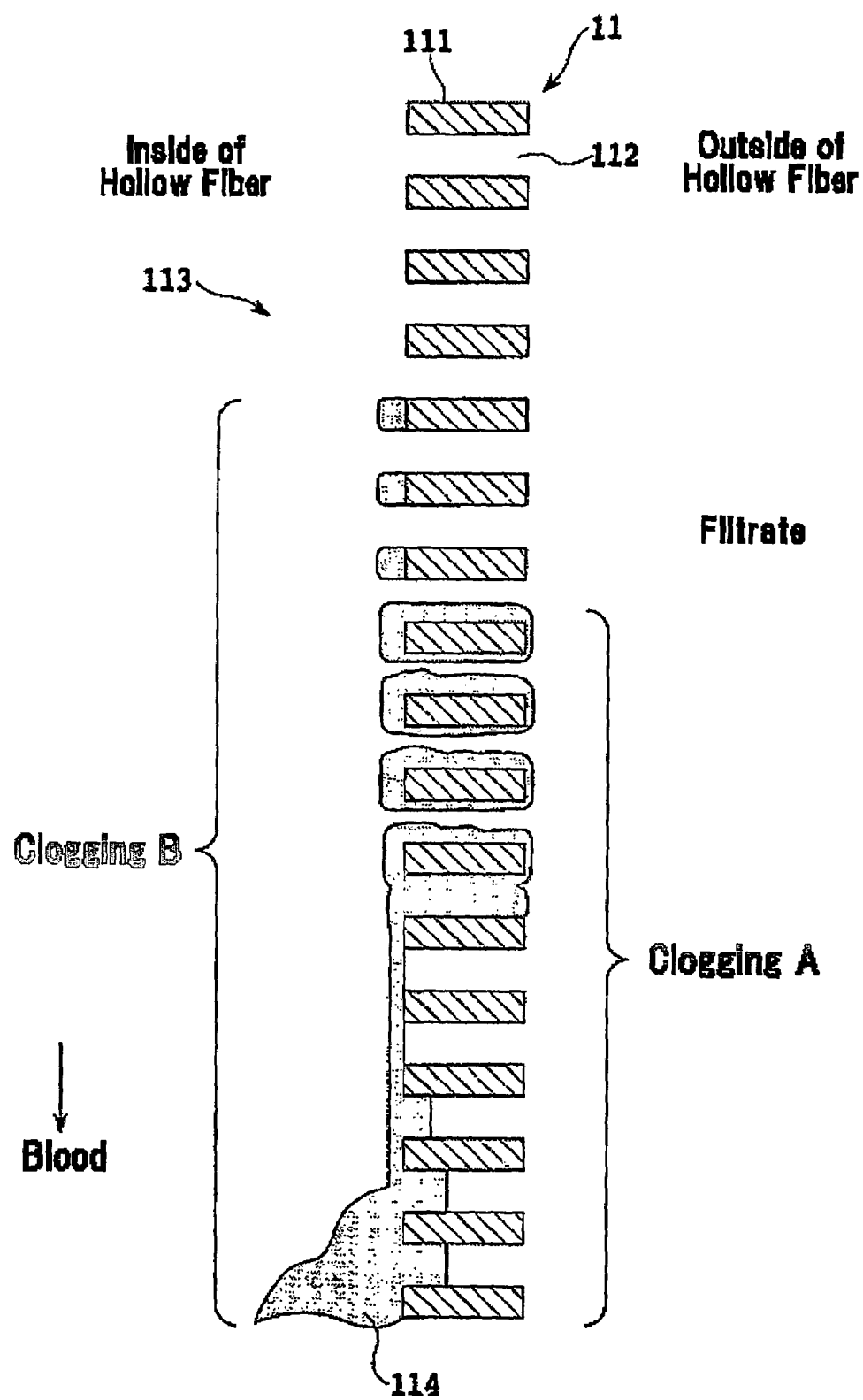
FIG. 5 is a view to explain a clogging in vertical direction and in lateral direction.

As shown in FIG. 5, adhesion of substances onto the membrane surface of the hollow-fiber causes not only clogging (lateral clogging) A of fine hole 112 of the hollow-fiber membrane 111 of the hollow-fiber 11 but also clogging of the inside 113 of hollow-fiber (vertical clogging) B due to a narrowing of the inside 113 of hollow-fiber simultaneously. The clogging (vertical clogging) B of the inside 113 of the hollow-fiber is only caused by adhesion of substances (e.g., protein, fibrin, blood platelets, blood cells, medicine) 114 onto the surface of the hollow-fiber membrane 111. In contrast thereto, the clogging (lateral clogging) A of fine hole 112 of the hollow-fiber membrane 111 is caused by adhesion of the substances 114 not only onto the surface of the hollow-fiber membrane 111 but also into the fine hole 112 of the hollow-fiber membrane 111. In addition, a waste liquid (filtrate or dialyzing fluid) exists outside the hollow-fiber.

The clogging (vertical clogging) B inside the hollow-fiber leads to the reduction in the blood flow rate and the reduction in the substance removal capability by diffusion. The reduction in the blood flow rate facilitates adhesion of substances onto the membrane and makes clogging more likely to occur. Complete clogging of the inside of hollow-fiber not only makes it impossible to remove substances of the hollow-fiber at the outlet from the clogged portion but also allows the blood to remain in the filter (residual blood) at the end of blood purification, and may results in a blood loss of the patient.

The clogging (lateral clogging) A of fine hole of the hollow-fiber membrane leads to the reduction in substance removal capability (clearance), and further has a risk of sucking a blood cell, which has a larger diameter than the fine hole and does not pass through the fine hole, by a strong negative pressure and causing destruction of the blood cell (hemolysis, etc.). The removal capability to a waste liquid in filtering or dialysis means ease of passing of a substance to a waste liquid when the substance with a molecular weight as a reference is passed through the filter, and decreases when the clogging deteriorates.

Portions of clogging of the membrane and the degree of clogging are determined by 1) conditions for executing blood purification such as type of a filter, flow rate setting, type and dosage amount of anti-coagulant, type of substitution liquid and dialyzing fluid, 2) clinical condition of the patient, 3) medical treatment conditions such as blood transfusion, medicine, medical treatment, etc. Herein, adhesion of substances onto the surface of the hollow-fiber membrane is related to the vertical clogging and lateral clogging, while adhesion of substances inside the fine hole of the hollow-fiber membrane is related to the lateral clogging.

In a method of detecting a filter clogging in the present invention, it is necessary to continuously measure the pressure inside the filter circuit and obtain the pressure information. In other words, in this embodiment, variations in pressure information with time are obtained by measuring at least one of the blood inflow portion pressure, for example, a pressure measured in a blood inflow portion-side drip-chamber located between a blood roller pump and the filter (blood inflow portion pressure (arterial pressure: Pa)), the blood outflow portion pressure, for example, a pressure measured in a blood outflow portion-side drip-chamber located downstream of the filter (blood outflow portion pressure (venous pressure: Pv)), the filtrate (or dialyzing fluid) inflow portion pressure, for example, a pressure measured outside the hollow-fiber on the blood inflow portion side of the filter (filtrate outflow portion pressure: Pf1) and the filtrate (or dialyzing fluid) outflow portion pressure, for example, a pressure measured outside the hollow-fiber on the blood outflow portion side of the filter (filtrate inflow portion pressure: Pf2).

Figure 6:
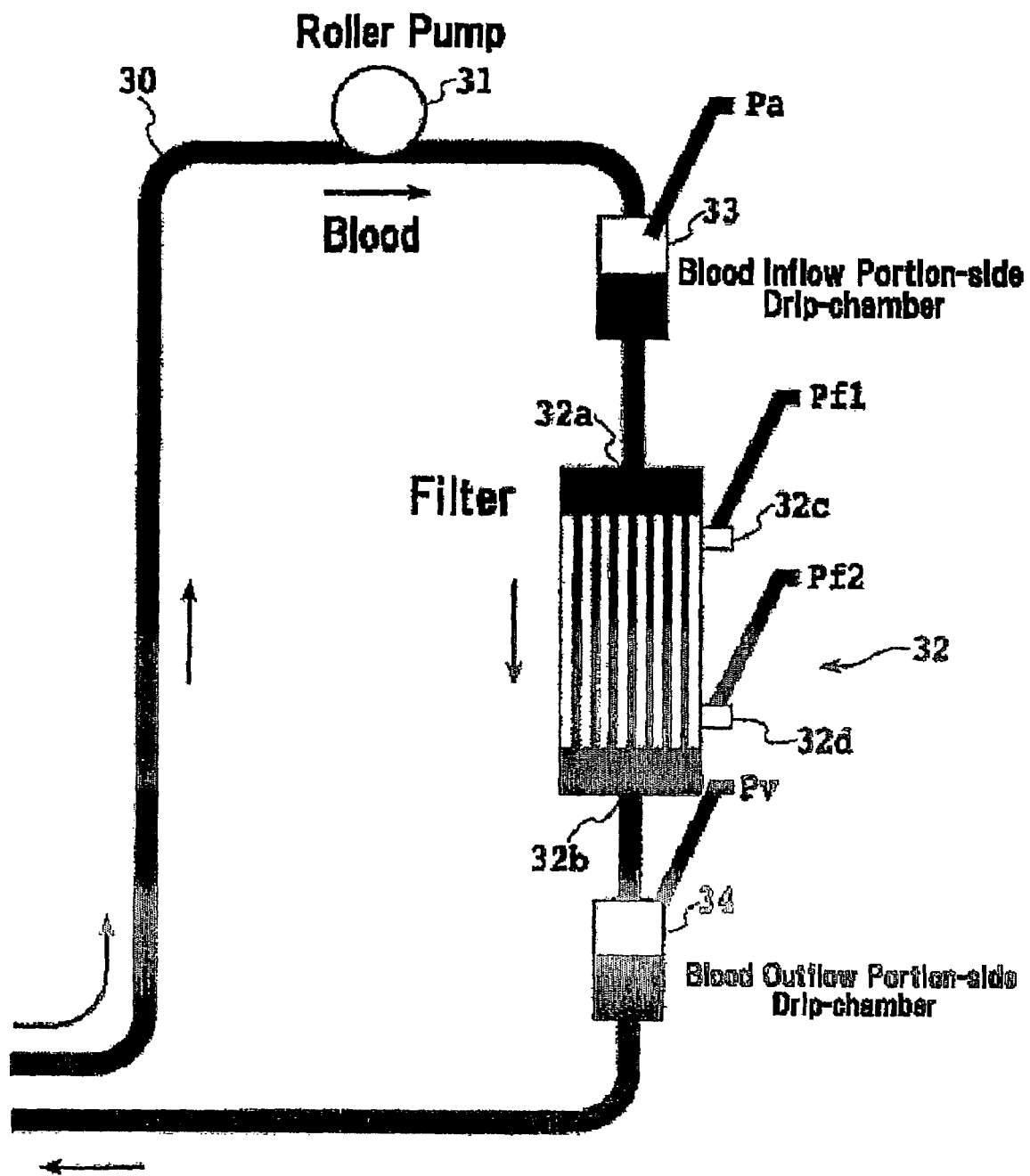
FIG. 6 is a view to explain a portion of measuring the pressure that is used in a method according to the present invention.

Portions for measuring Pa, Pv, Pf1 and Pf2 will be described below. Pa, Pv, Pf1 and Pf2 are measured at the portions shown in FIG. 6. In FIG. 6, a roller pump 31 is connected to a circulation path 30 along which the blood flows. This roller pump 31 circulates blood (bodily fluid) through the circulation path 30 outside the body. The circulation path 30 is provided with a filter 32 that filters the blood. The filter 32 is provided with a blood inflow portion 32a and blood outflow portion 32b, and further provided with a coupler 32c of blood inflow portion and a coupler 32d of blood outflow portion which serve as the inlet and outlet of dialyzing fluid and waste liquid. The couplers 32c and 32d are connected to their respective tubes (not shown), and the pressures in the tubes become the filtering pressure (Pf1) of the blood inflow portion and the filtering pressure (Pf2) of the blood outflow portion respectively.

Further, a blood inflow portion-side drip-chamber 33 is provided upstream of the filter 32 on the circulation path 30. Furthermore, a blood outflow portion-side drip-chamber 34 is provided downstream of the filter 32 on the circulation path 30. In this embodiment, the pressures Pa and Pv of the blood inflow portion 32a and blood outflow portion 32b of the filter 32 are measured at the blood inflow portion-side drip-chamber 33 and blood outflow portion-side drip-chamber 34, respectively. However, when respective pressures in the blood inflow portion 32a and blood outflow portion 32b of the filter 32 can be measured, Pa and Pv may be measured at any portions other than the blood inflow portion-side drip-chamber 33 and blood outflow portion-side drip-chamber 34.

In such a configuration, a blood inflow portion pressure (arterial pressure: Pa) is measured at the blood inflow portion-side drip-chamber 33, a filtering pressure (Pf1) of the blood inflow portion is measured at the tube connected to the coupler 32c of blood inflow portion, and a filtering pressure (Pf2) of the blood outflow portion is measured at the tube connected to the coupler 32d of blood outflow portion.

In addition, methods for measuring pressures at the respective portions are the same as a general method for measuring a pressure in filter clogging detection. Further, the pressure information may be corrected as appropriate in consideration of the osmotic information of blood (colloid osmotic pressure of blood).

In the method for detecting a filter clogging of the present invention, it is necessary to analyze variations with time in pressures measured as described above, i.e. pressure waveforms. The pressure waveform is data obtained by continuously measuring a pressure value at intervals of extremely short time such as 100 times per second.

As a method of analyzing thus obtained pressure waveform, there is a method for transforming into frequency/amplitude using Fast Fourier Transform (FFT), as spectral analysis of pressure waveform. For example, time-series signals of the pressure (sampling frequency: 100 Hz) are subjected to Fast Fourier Transform in 4096 samplings (approximately 41 seconds, resolution: 0.025 Hz). The result is shown in FIG. 7.

Figure 7:
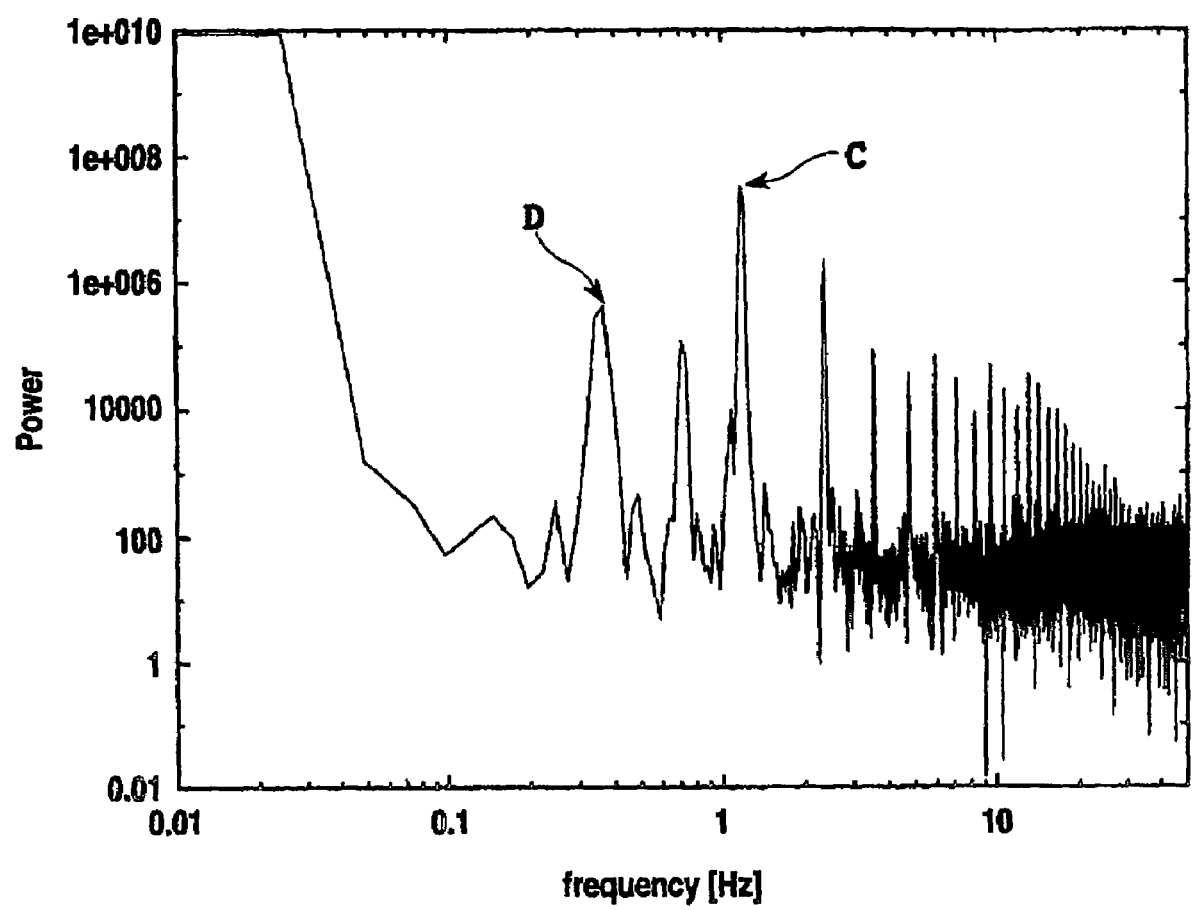
FIG. 7 is a view to explain to identification of basic frequency.

FIG. 7 shows the result of FFT analysis of the blood inflow portion pressure (Pa) in filtering with Qb of 100 ml/min. and Qf of 15 ml/min., where the horizontal axis indicates the frequency and the vertical axis indicates the power as described later.

A method will be described below for detecting a status of clogging using transformed values in the FFT analysis.

First, used among transformed values subjected to Fourier Transform are a frequency (basic frequency C of the blood pump in FIG. 7) corresponding to pulsation of the pump apparatus (blood pump) to feed blood to the filter, a frequency (basic frequency D of the filtering pump in FIG. 7) corresponding to pulsation of the pump apparatus (filtering pump) to feed out the filtrate (or dialyzing fluid), or a transformed value corresponding to either frequency.

Figure 8:
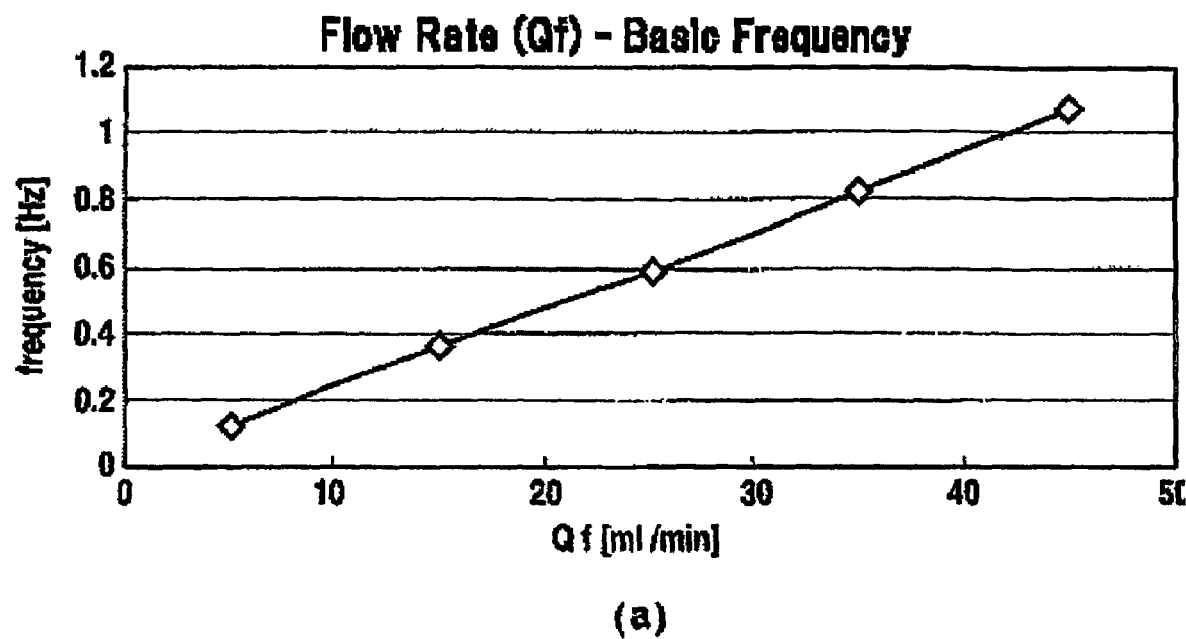
FIG. 8 is a view showing flow rate/basic frequency characteristics.
Figure 8:
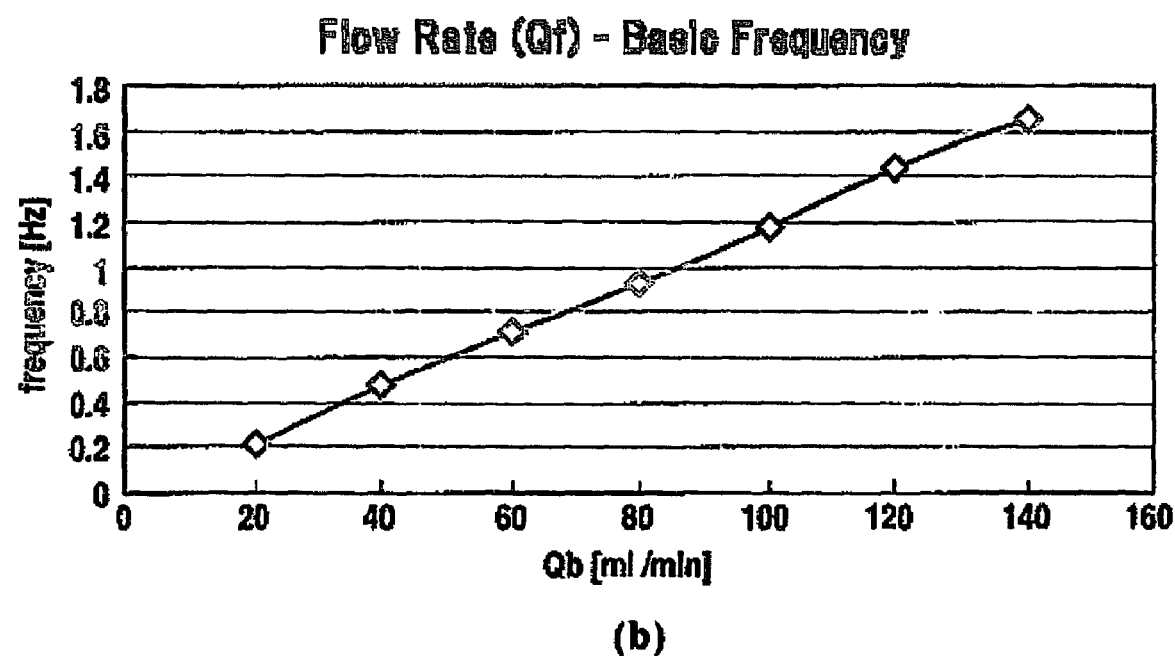

FIG. 8(a) shows the relationship between the basic frequency and flow rate Qf of the blood pump, and FIG. 8(b) shows the relationship between the basic frequency and flow rate Qb of the filtering pump.

The amplitude spectrum and power spectrum in each basic frequency are calculated. The power is a value of square of the amplitude spectrum, and is calculated using values of a real part a and imaginary part b of a signal obtained from Fast Fourier Transform with the following equation:

$$\text{Power} = a^2 + b^2 \tag{1}$$

As another method, there is calculated a gradient of frequency/amplitude, i.e. phase corresponding to each pump apparatus. In this case, the phase is calculated using the values of the real part a and imaginary part b with the following equation:

$$\text{Phase difference} = \tan^{-1} b/a \tag{2}$$

In this embodiment, a status of clogging is detected using the amplitude, power or phase in some pressure measuring portion as an indicator. Further, the clogging is detected using the ease of propagation of amplitude/power (ratio of amplitude/power) between a point and another point or a phase difference between a point and another point.

Further, it may be possible to adopt a ratio of amplitude/power or phase difference corresponding to TMP (Trans-Membrane Pressure) that is a membrane pressure difference. With respect to TMP, for example, equations (3) to (5) as described below can be used. Using either TMP1, TMP2 or TMP is determined as appropriate according to the purpose.

$$TMP1 = Pa - Pf1 \tag{3}$$

$$TMP2 = Pv - Pf2 \tag{4}$$

$$TMP3 = (Pa + Pv)/2 - (Pf1 + Pf2)/2 \tag{5}$$

Power ratios $G(\omega)TMP1$, $G(\omega)TMP2$ and $G(\omega)TMP3$ respectively corresponding to TMP1 to TMP3 are obtained using following equations.

$$G(\omega)TMP1 = \frac{Power_{Pf1(\omega)}}{Power_{Pa(\omega)}} \tag{6}$$

$$G(\omega)TMP2 = \frac{Power_{Pf2(\omega)}}{Power_{Pv(\omega)}} \tag{7}$$

$$G(\omega)TMP3 = \frac{(Power_{Pf1(\omega)} + Power_{Pf2(\omega)})/2}{(Power_{Pa(\omega)} + Power_{Pv(\omega)})/2} \tag{8}$$
$$= \frac{Power_{Pf1(\omega)} + Power_{Pf2(\omega)}/2}{Power_{Pa(\omega)} + Power_{Pv(\omega)}/2}$$

Similarly, phase differences $\angle G(\omega)TMP1$, $\angle G(\omega)TMP2$ and $\angle G(\omega)TMP3$ respectively corresponding to TMP1 to TMP3 are obtained using following equations.

$$\angle G(\omega)TMP1 = \angle Pf1(\omega) - \angle Pa(\omega) \tag{9}$$

$$\angle G(\omega)TMP2 = \angle Pf2(\omega) - \angle Pv(\omega) \tag{10}$$

$$\angle G(\omega)TMP3 = \frac{\angle Pf1(\omega) + \angle Pf2(\omega)}{2} - \frac{\angle Pa(\omega) + \angle Pv(\omega)}{2} \tag{11}$$

For example, the amplitude, power, phase, ratio of amplitude and/or power, and/or phase difference with respect to the basic frequency of the blood pump can be used to detect clogging in the direction of blood flow (vertical direction), while the amplitude, power, phase, ratio of amplitude and/or power, and/or phase difference with respect to the basic frequency of the filtering pump can be used to detect clogging in the direction of from blood to filtrate (lateral direction).

Examples of clogging detection in the clinical model and clogging model will be described below.

As the clinical model and clogging model, various kinds of sustained blood filters (manufactured by Asahi Medical CO., Ltd) described as below were used as a filter, and ACH-10 (manufactured by Asahi Medical CO., Ltd) was used as a sustained blood purification apparatus.

1) Clinical Model
Filter: APF-06S(Membrane area: 0.6 m²)
Filtering rate: Qb=100 ml/min., Qf=15 ml/min.
2) Combined clogging model filter (vertical and lateral clogging)
Filter:
  APF-10S(Membrane area: 1.0 m²): Without vertical and lateral clogging
  APF-06S(Membrane area: 0.6 m²): With light to medium vertical and lateral clogging
  APF-03S(Membrane area: 0.3 m²): With strong vertical and lateral clogging Circuit and pressure measuring portion: V chamber forward return model
Blood and filtrate: water
Filtering rate: Qb=100 ml/min., Qf=15 ml/min.
3) Lateral (clogging of fine hole of hollow-fiber) clogging filter model
Filter:
  APF-03S(Membrane area: 0.3 m², Filtering coefficient of Prolactin (Mw: 22000): 0.43, without lateral clogging)
  PAN-03D(Membrane area: 0.3 m², Filtering coefficient of Prolactin (Mw: 22000): 0.16, with light to medium lateral clogging)
Circuit and pressure measuring portion: Tank return model
Blood and filtrate: Water
Filtering rate: Qb=100 ml/min., Qf=15 ml/min.

Figure 9:
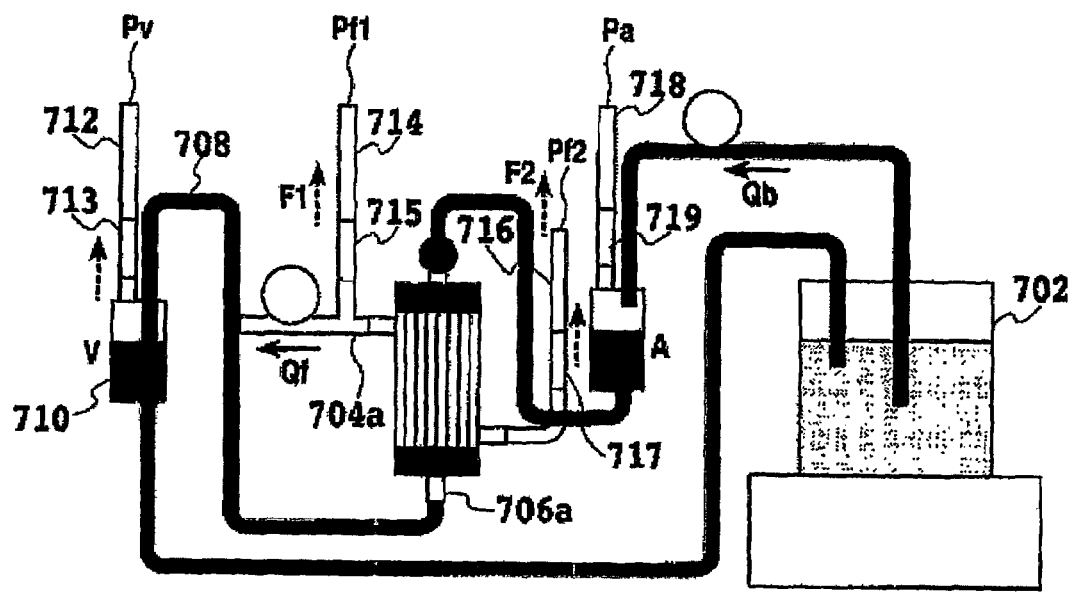
FIG. 9 is a view showing a configuration of circuit arrangement used in examples of the present invention.
Figure 9:
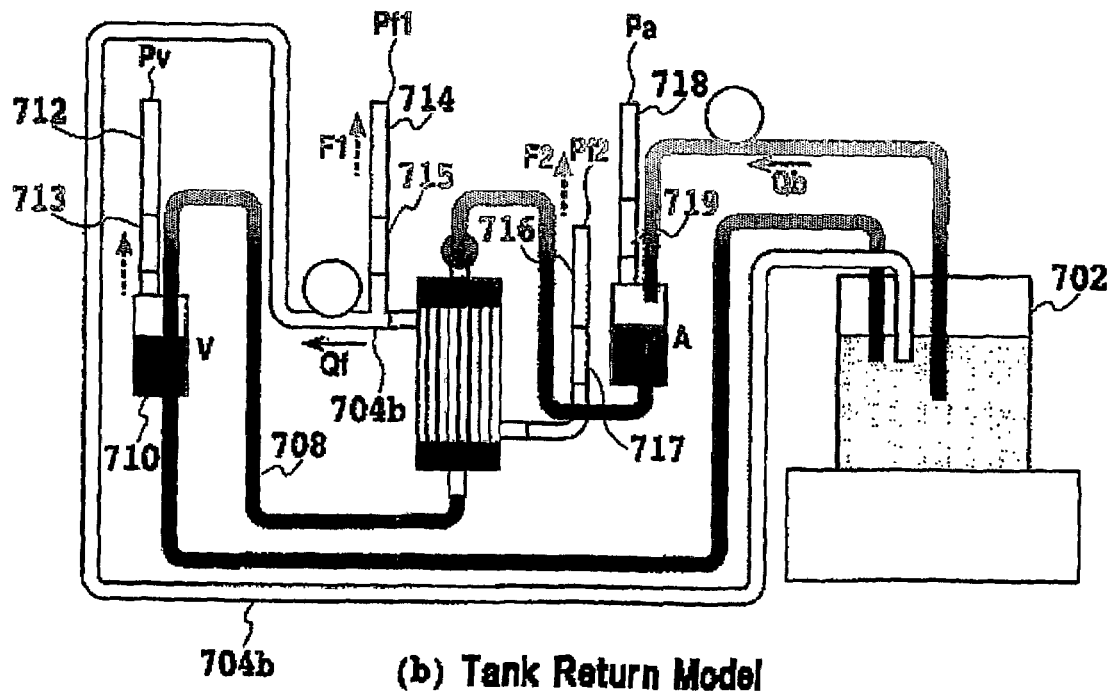

As blood and blood circuit, a blood circuit (CHF-400N: Asahi Medical CO., Ltd.) was used. In the clogging model, arrangements of V chamber forward return model and tank return model were used as shown in FIGS. 9(a) and 9(b). In the V chamber forward return mode, as shown in FIG. 9(a), a filtering waste tube 704a is connected to a blood outflow tube (circulation path) 708 from a blood outflow portion 706 a of the filter. In contrast thereto, in the tank return model, as shown in FIG. 9(b), a filtering waste tube 704b is returned to a blood tank 702. Used in the clinical model was an arrangement according to the circuit arrangement of the tank return model, where the blood circuit was connected to a human body, the filtrate circuit was connected to the filtrate tank, and the filtering waste liquid was discharged outside the system. Further, in the clinical model, a fluid replacement tube was connected to the blood outflow tube 708 upstream of a blood outflow portion-side drip-chamber 710 of the tank return model in FIG. 9(b) via a fluid replacement pump.

Pressures were measured in positions as shown in FIGS. 9(a) and 9(b) using pressure sensors. The pressure sensors were spaced from predetermined positions to measure Pa, Pv, Pf1 and Pf2 via glass pipes 713, 715, 717 and 719 each with a diameter of 5 mm and length of 69 cm and pressure-resistant tubes 712, 714, 716 and 718 each with a diameter of 2 mm and length of 180 cm, respectively.

The obtained pressure information was analyzed using the methods as described above, and power, phase, power ratio and phase difference were calculated with respect to each frequency. The basic frequency of the blood pump was 1.17 Hz, and the basic frequency of the filtrate pump was 0.36 Hz.

Figure 10:
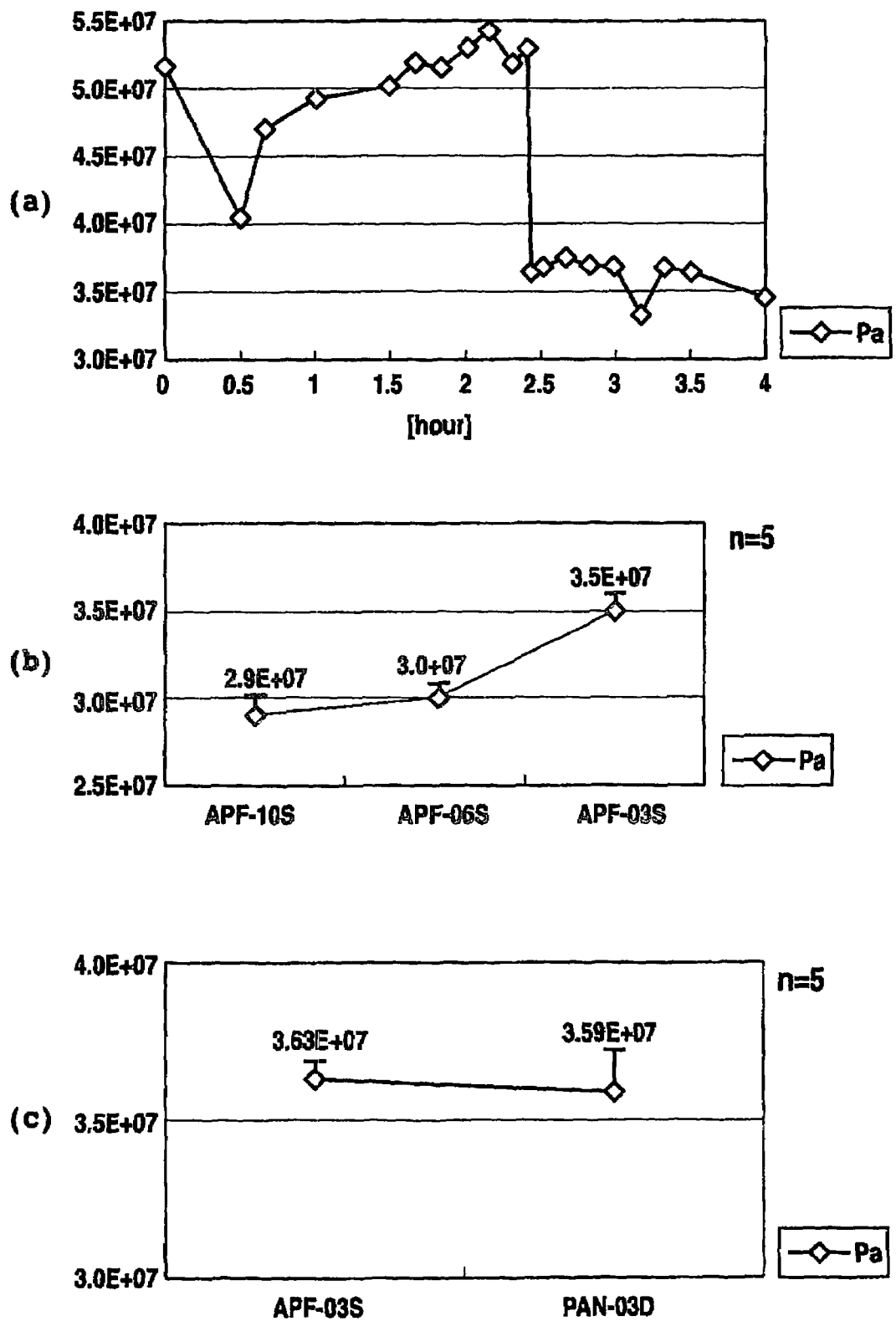
FIG. 10 is a view showing calculation results of power of Pa with respect to the blood pump frequency in each model.

FIGS. 10(a) to 10(c) show calculation results of power of Pa with respect to the blood pump frequency in the models. FIG. 10(a) shows the results in the clinical model, FIG. 10(b) shows the results in the combined clogging model, and FIG. 10(c) shows the results in the lateral clogging model.

Figure 11:
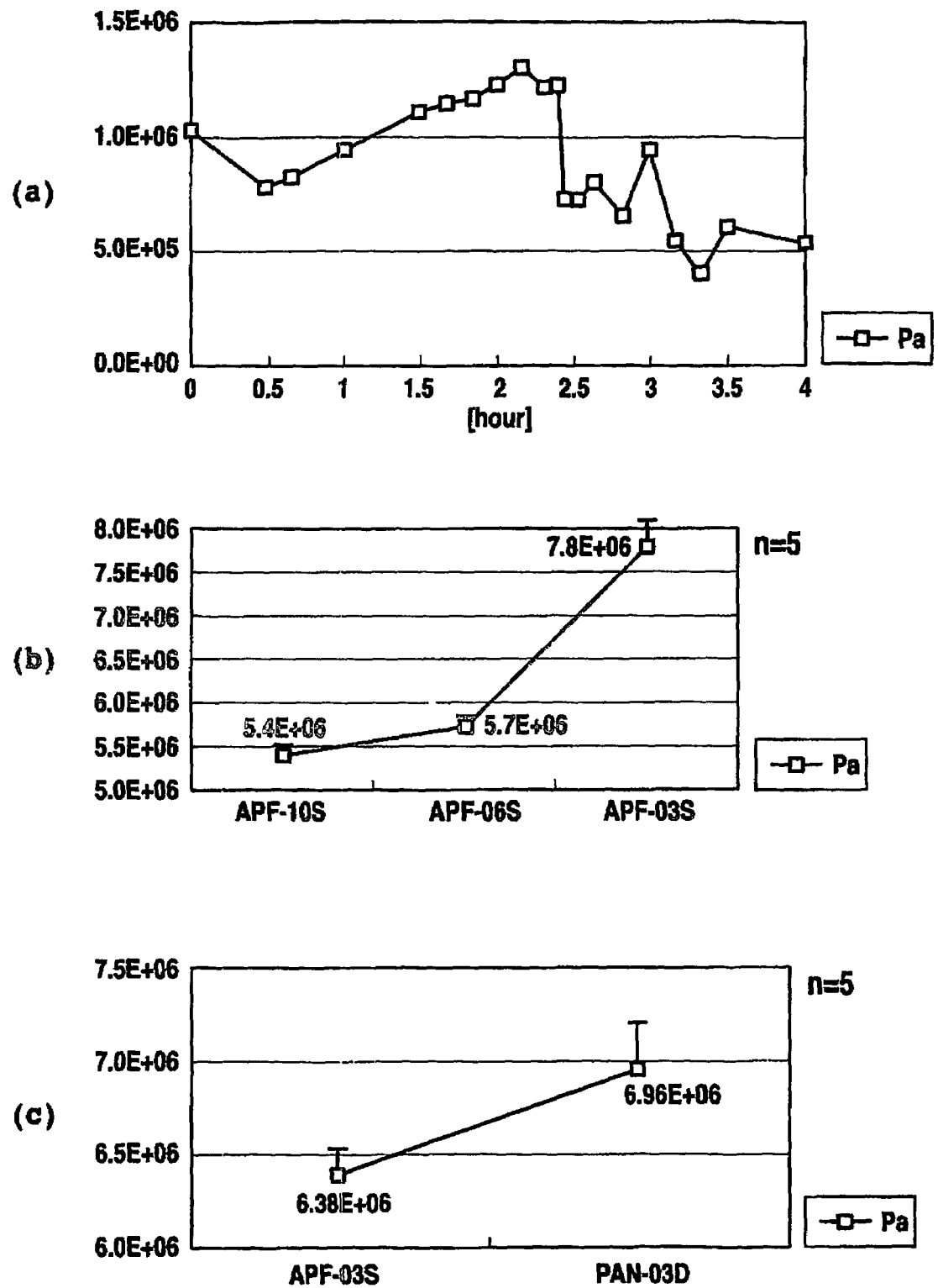
FIG. 11 is a view showing calculation results of power of Pv with respect to the blood pump frequency in each model.
Figure 12:
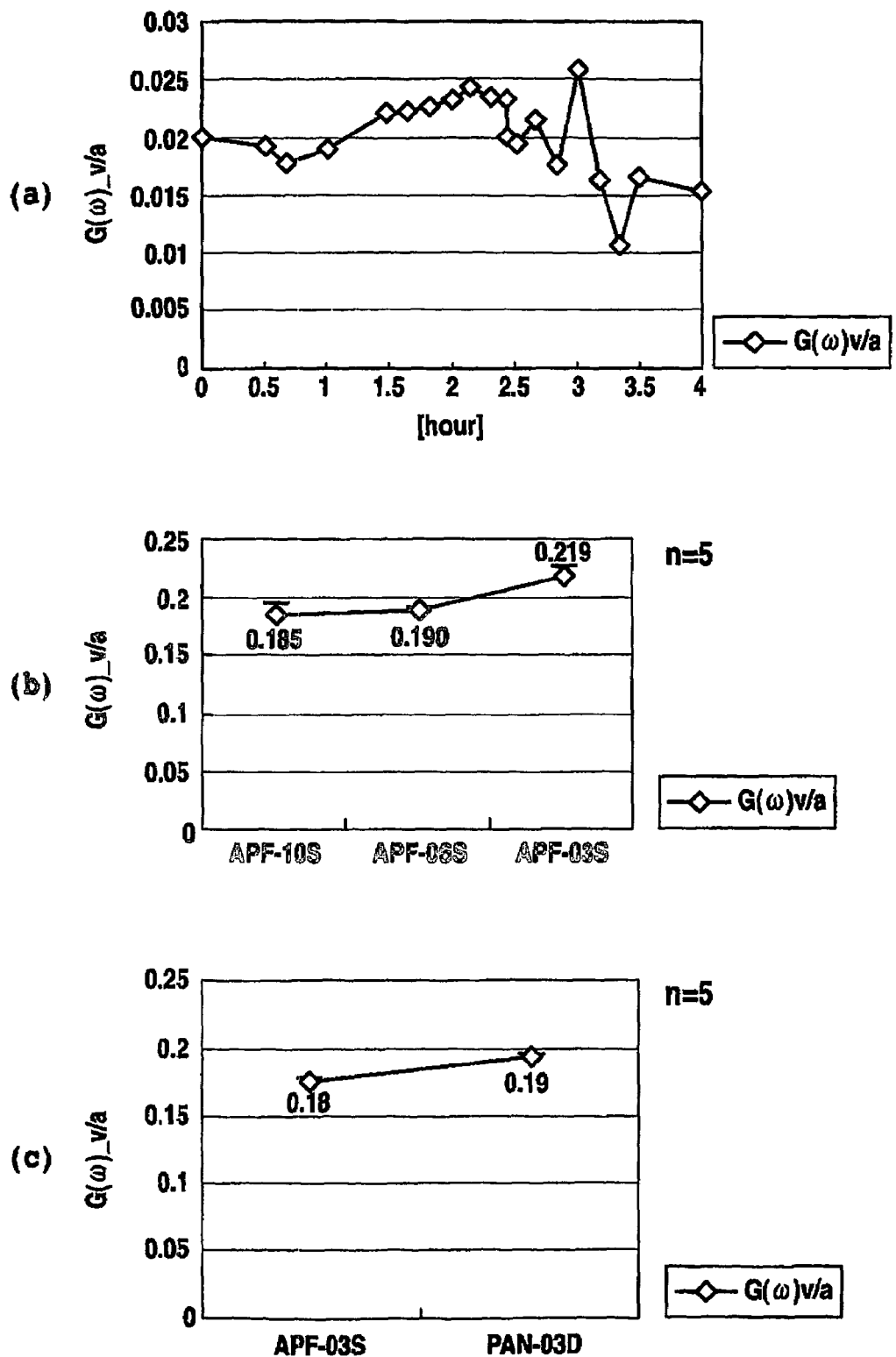
FIG. 12 is a view showing calculation results of power ratio $G(\omega)v/a$ between Pa and Pv with respect to the blood pump frequency in each model.

FIGS. 11(a) to 11(c) show calculation results of power of Pv. FIG. 11(a) shows the results in the clinical model, FIG. 11(b) shows the results in the combined clogging model, and FIG. 11(c) shows the results in the lateral clogging model. FIGS. 12(a) to 12(c) show calculation results of power ratio between Pa and Pv, i.e. $G(\omega)v/a$. FIG. 12(a) shows the results in the clinical model, FIG. 12(b) shows the results in the combined clogging model, and FIG. 12(c) shows the results in the lateral clogging model.

The power of Pa does not vary in the lateral clogging model, and therefore, may represent the vertical clogging. Meanwhile, the power of Pv represents vertical and lateral clogging. Both power values of Pa and Pv are indicated with high resolution as compared to pressure actual measurement values, their calculation values (TMP), etc. Further, in either clogging model, as shown in FIGS. 12(a) to 12(b), the power ratio between Pa and Pv increases corresponding to increases in clogging degree.

Figure 13:
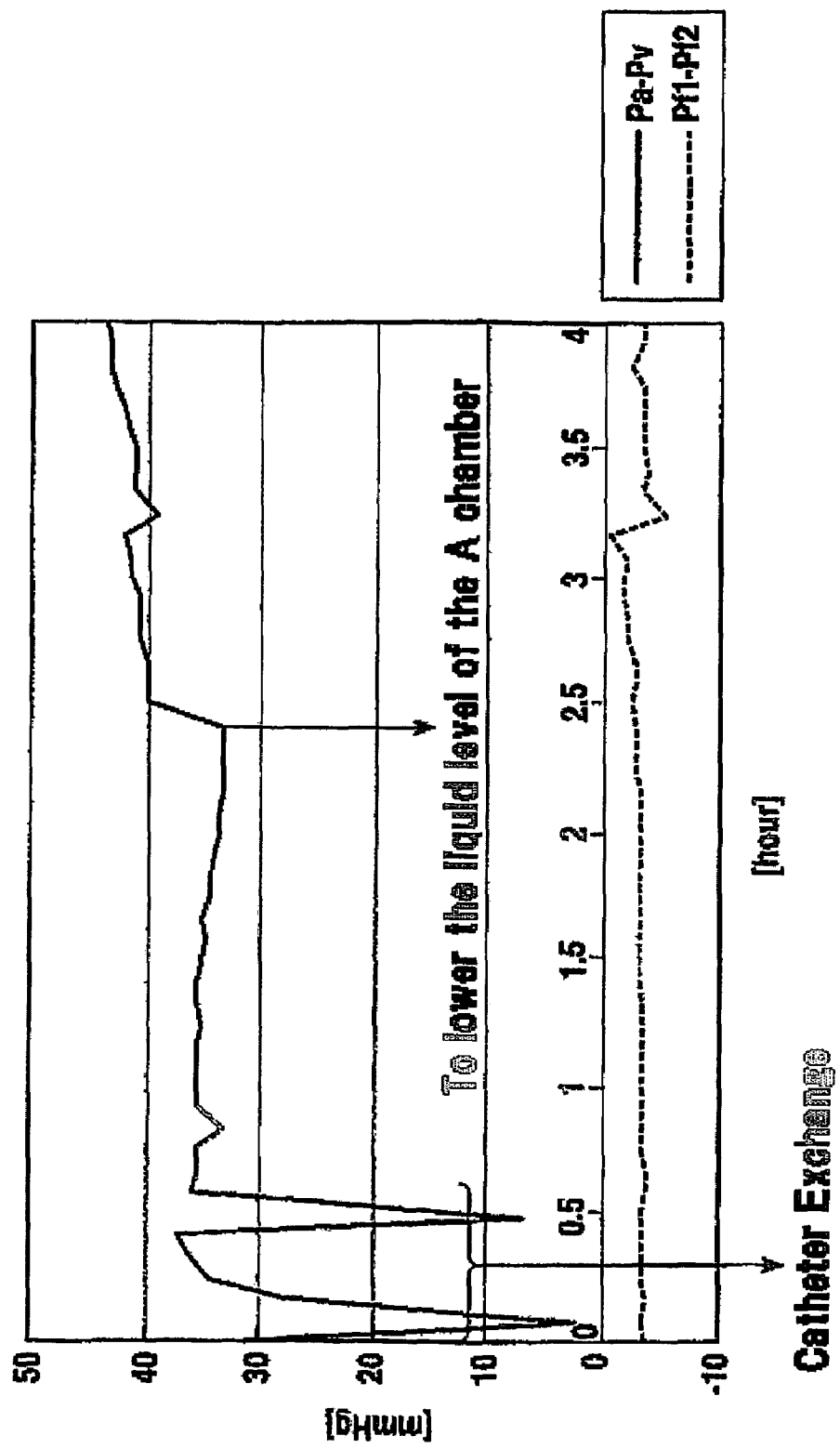
FIG. 13 is a view showing calculation results of Pa–Pv and Pf1–Pf2 calculated from actual pressure measurement values in a clinical model.

FIG. 13 shows calculation results of pressure calculation values Pa−Pv and Pf1−Pf2 calculated from the actual pressure measurement values in the clinical model.

It is understood from FIGS. 10(a), FIG. 11(a) and FIGS. 12(a) that power of Pa and Pv or the power ratio $G(\omega)v/a$ in the clinical model increase with time and then decrease, and that the peak values (about 2.1 hours later) appear before the pressure calculation value Pa−Pv increases as shown in FIG. 13. This indicates that a dull waveform may develop when the gel layer inside the membrane increases, further blood clot occurs, and the vertical clogging is more than a certain degree. Accordingly, in this embodiment, there is a possibility that clogging can be detected that cannot be detected by actual pressure measurement values or calculation value.

Figure 14:
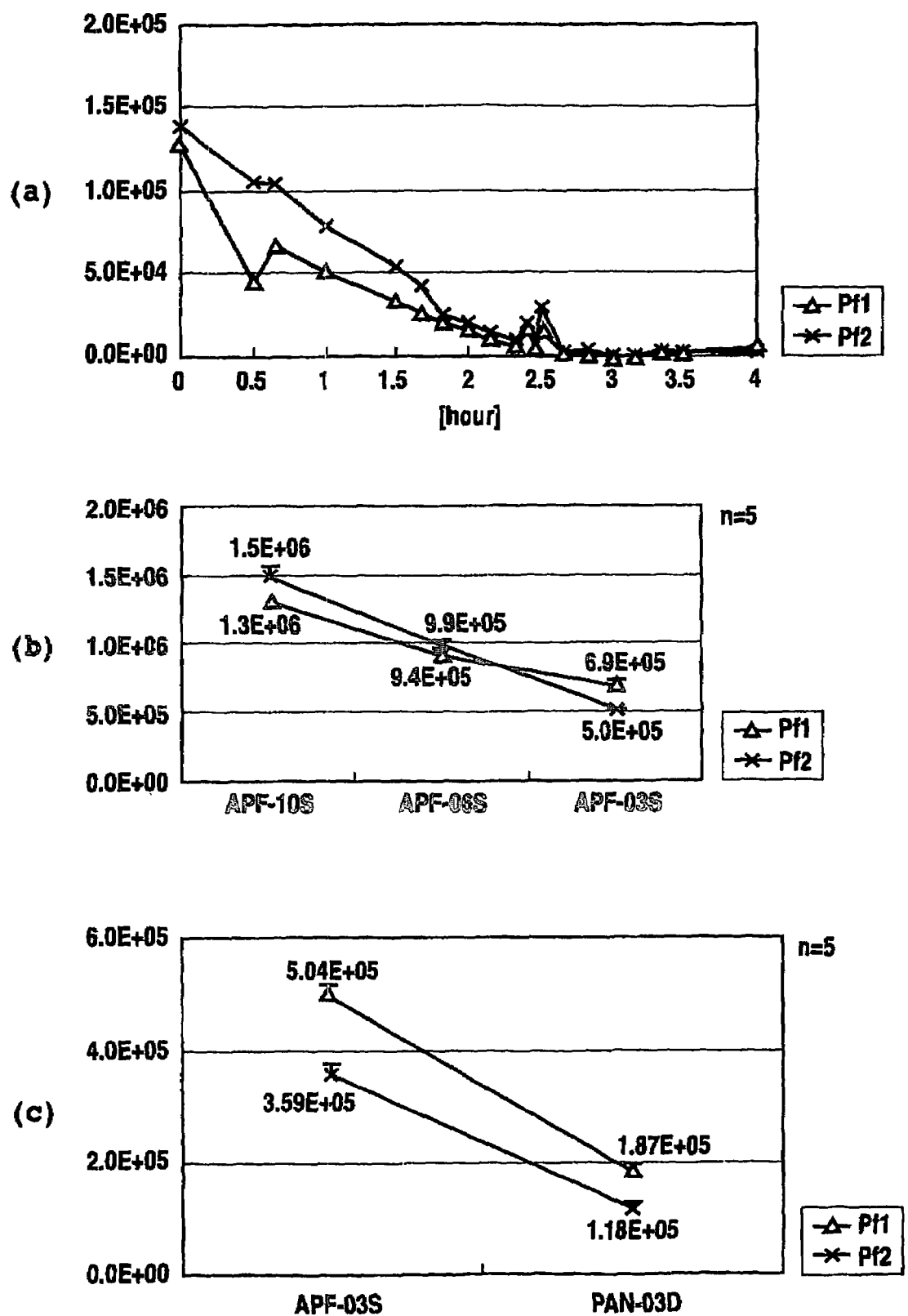
FIG. 14 is a view showing calculation results of power of Pf1 and Pf2 with respect to the blood pump frequency in each model.
Figure 15:
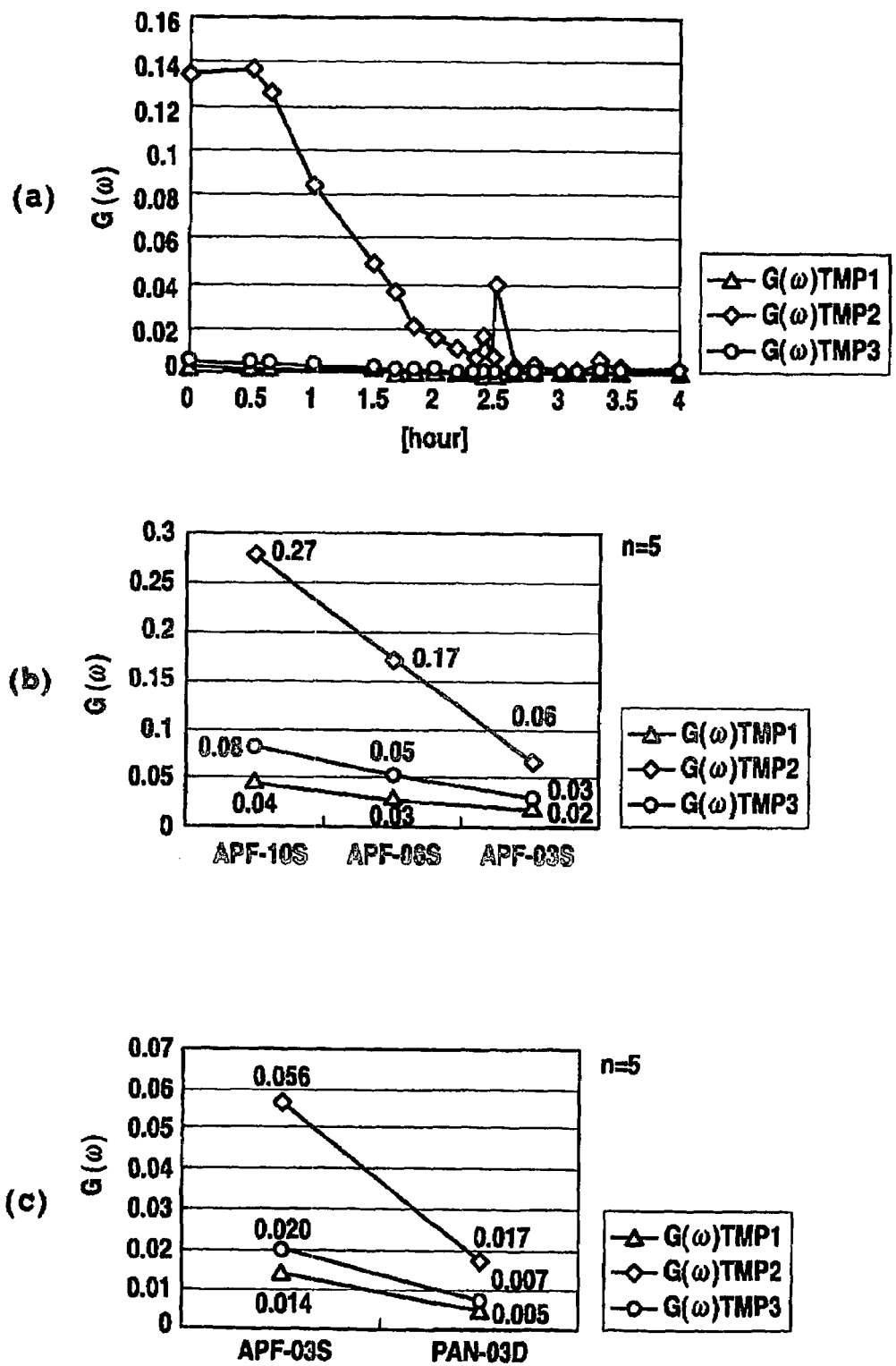
FIG. 15 is a view showing calculation results of power ratios $G(\omega)TMP1$, $G(\omega)TMP2$ and $G(\omega)TMP3$ respectively corresponding to TMP1, TMP2 and TMP3 with respect to the blood pump frequency in each model.

FIGS. 14(a) to 14(c) show calculation results of power of Pf1 and Pf2 with respect to the blood pump frequency in the models. FIG. 14(a) shows the results in the clinical model, FIG. 14(b) shows the results in the combined clogging model, and FIG. 14(c) shows the results in the lateral clogging model. FIGS. 15(a) to 15(c) show calculation results of power ratios $G(\omega)$TMP1, $G(\omega)$TMP2 and $G(\omega)$TMP3 respectively corresponding to TMP1, TMP2 and TMP3. FIG. 15(a) shows the results in the clinical model, FIG. 15(b) shows the results in the combined clogging model, and FIG. 15(c) shows the results in the lateral clogging model.

It is understood that the power decreases when passed through the membrane (fine hole) in all the models. There is a possibility that such a state is detected that a dull reduction in waveform is extreme which occurs when the vertical clogging is more than a certain degree. In the lateral clogging model, power of Pf1 and Pf2 and power ratios corresponding to TMP1, TMP2 and TMP3 decrease as compared to the normal model. In the clinical model, power of Pf1 and Pf2 and power ratios corresponding to TMP1, TMP2 and TMP3 decrease with time.

Figure 16:
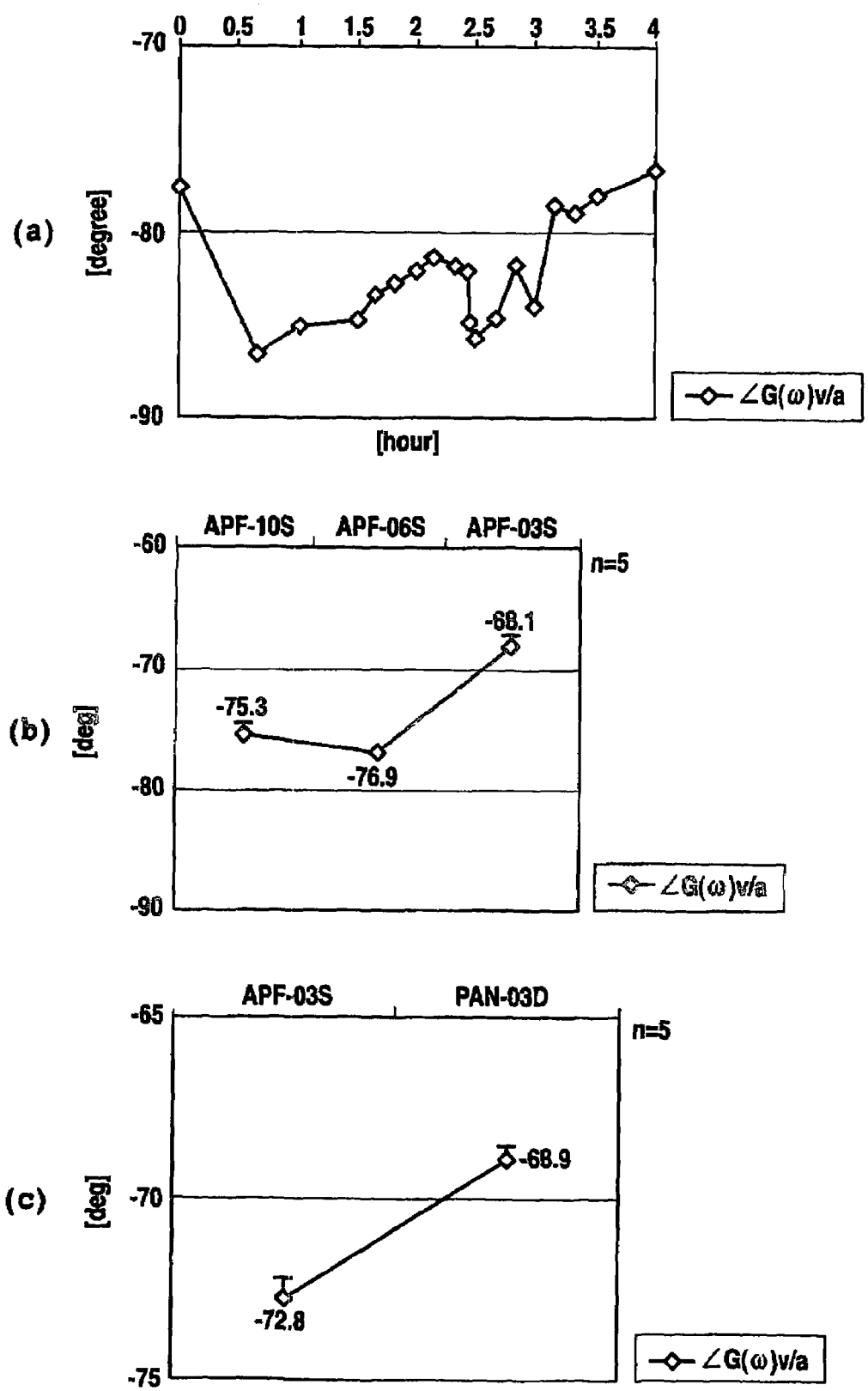
FIG. 16 is a view showing calculation results of phase difference $\angle G(\omega)$ V/a between Pa and Pv with respect to the blood pump frequency in each model.

FIGS. 16(a) to 16(c) show calculation results of phase difference $\angle G(\omega)$ between Pa and Pv with respect to the blood pump frequency in the models. FIG. 16(a) shows the results in the clinical model, FIG. 16(b) shows the results in the combined clogging model, and FIG. 16(c) shows the results in the lateral clogging model.

There is no vertical phase difference in the clogging models. Meanwhile, in the clinical model, vertical phase difference $\angle G(\omega)v/a$ increases with time, it is thus suggested that the gel layer increases inside the hollow-fiber, further blood clot occurs and that ease of propagation of vibration is affected as compared to liquid state, and there is a possibility of capable of detecting a status of clogging that cannot be detected by actual pressure measurement value or the like.

Figure 17:
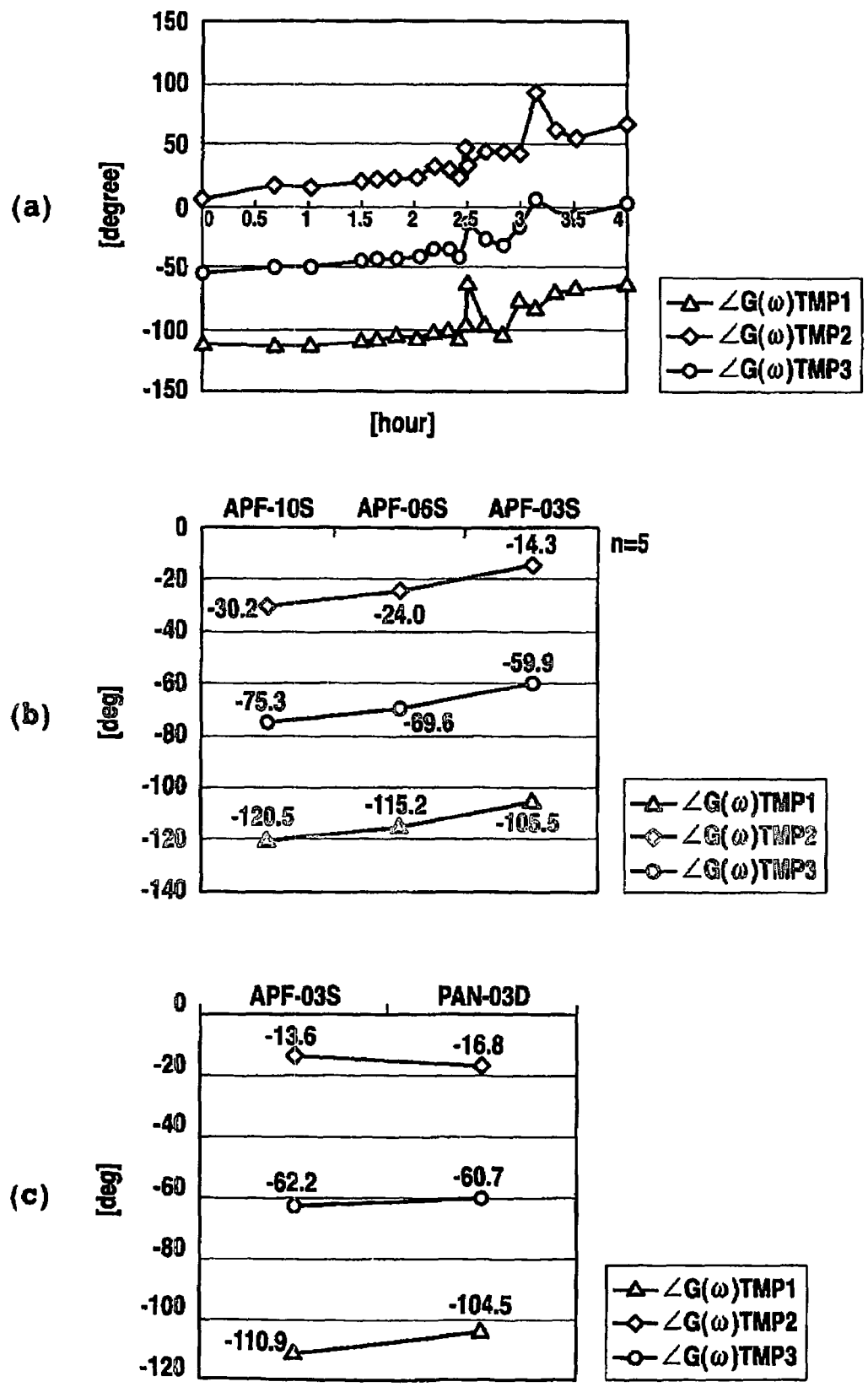
FIG. 17 is a view showing calculation results of phase differences $\angle G(\omega)$ TMP1, $\angle G(\omega)$ TMP2 and $\angle G(\omega)$ TMP3 respectively corresponding to TMP1, TMP2 and TMP3 with respect to the blood pump frequency in each model.

FIGS. 17(a) to 17(c) show calculation results of phase differences $\angle G(\omega)$ TMP1, $\angle G(\omega)$ TMP2 and $\angle G(\omega)$ TMP3 respectively corresponding to TMP1, TMP2 and TMP3 with respect to the blood pump frequency in the models. FIG. 17(a) shows the results in the clinical model, FIG. 17(b) shows the results in the combined clogging model, and FIG. 17(c) shows the results in the lateral clogging model.

It is understood that $\angle G(\omega)$ TMP1 increases in the clogging model when the lateral clogging develops. Further, it is understood that $\angle G(\omega))$ TMP1, $\angle G(\omega)$ TMP2 and $\angle G(\omega)$ TMP3 that represent lateral phase differences increase with time in the clinical model.

As is apparent from the aforementioned calculation results, the power changes from increases to decreases and phase differences increase corresponding to increases in clogging in the blood flow direction. Meanwhile, when passed through the membrane, the power decreases, and the phase difference increases. By using the results, it is possible to detect a status of clogging with fewer effects of operation and with higher resolution than in using the pressure information, and to detect a detailed status of clogging that cannot be detected from the pressure information.

According to the present invention, other than the above-mentioned methods, examples used as a method of analyzing a pressure waveform are obtaining a differential curve of the pressure waveform, examining a variation rate of the pressure, and calculating a maximum increment rate and/or maximum decrement rate of the variation rate of the pressure in the pressure waveform, time taken for the variation rate to vary from zero to the maximum increment rate, and/or time taken for the variation rate to vary from zero to the maximum decrement rate. Further, it may be possible to calculate a time taken for the pressure in the pressure waveform to vary from a minimum value to a maximum value, or from a maximum value to a minimum value, rising time (time taken for the pressure to rise from a value that is the minimum value plus 10% of the amplitude to a value that is the minimum value plus 90% of the amplitude), falling time (time taken for the pressure to fall from a value that is the maximum value minus 10% of the amplitude to a value that is the maximum value minus 90% of the amplitude), and/or time duration of specific pressure. Moreover, it may be possible to use a ratio (or difference) in each indicator or a difference of time indicating pressure minimum value (or maximum value) between two points.

Further, while the pressure waveforms were analyzed at 30-minute intervals in the above-mentioned examples, it is possible to recognize variations in filter in more detail and readily when analyzing at several-ten-second intervals and calculating differences and ratios of the results.

Furthermore, the above-mentioned examples show examination results with respect to the basic frequency of the blood pump; it may be possible to examine with respect to the basic frequency of the filtering pump, dialysis pump, drain pump or other pump.

Moreover, the above-mentioned examples show examination results with respect to the basic frequency of the blood pump in transformed values obtained by Fast Fourier Transform. However, it may be possible to calculate total power of all frequency components, and checking the variations may detect variations in filter in more detail. Further, it may be possible to calculate total power of frequency components of integer times (for example, up to 5 times) of the basic frequency, or with respect to a noise component other than the frequency components of basic frequency and its integer-times frequency, power of high frequency component (HF power), power of low frequency component (LF power), ratio between LP power and HF power, ratio between HF power and total power, and/or ratio between LF power and total power, and checking respective variations may detect variations in filter in more detail.

Figure 18:
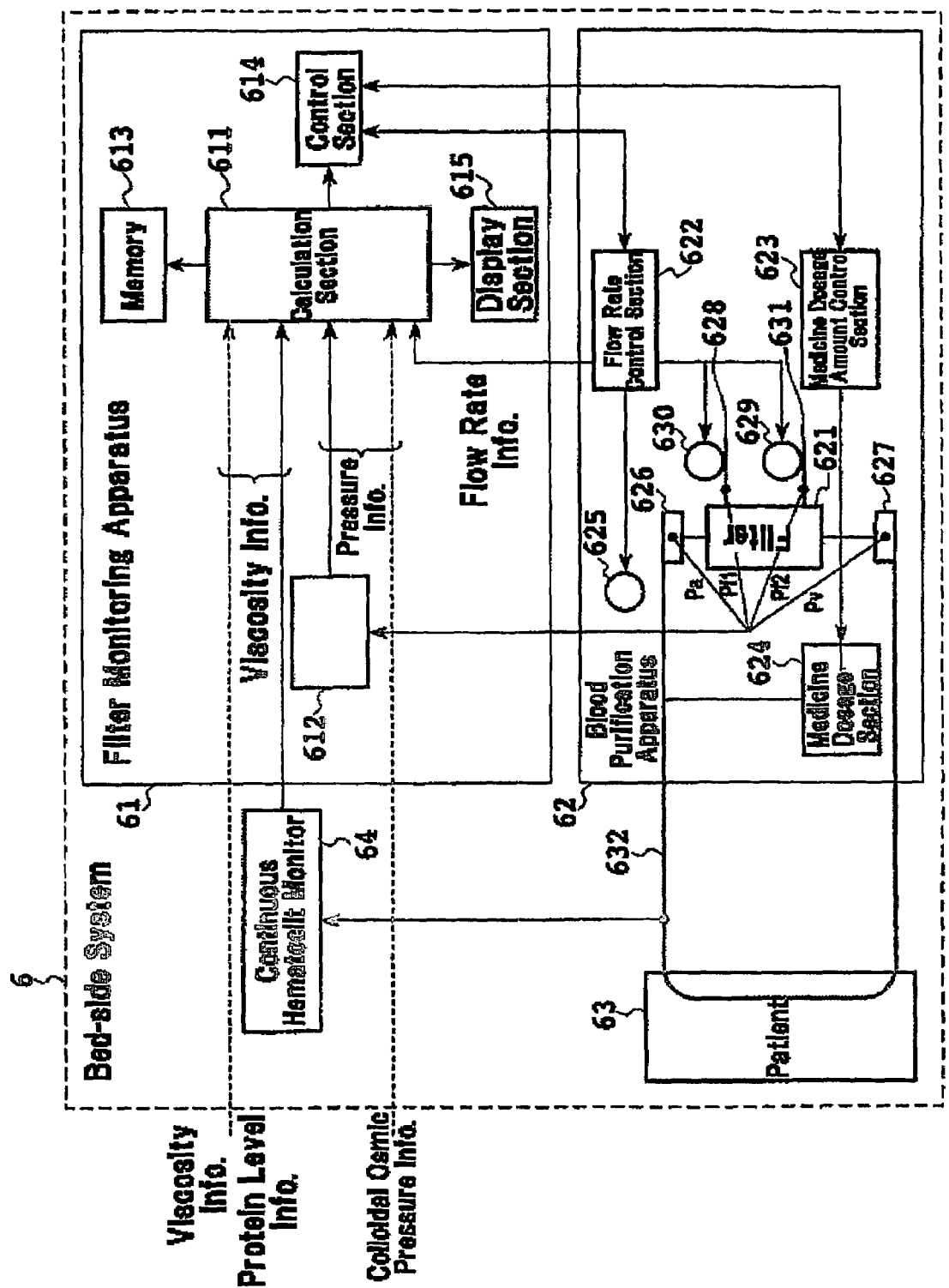
FIG. 18 is a view showing an arrangement of a bed-side system which implements a method according to the present invention.

A bed-side system that implements the method according to the present invention will be described below. The bed-side system 6 shown in FIG. 18 is composed in such a way that the flow rate of blood and dosage amount of medicine are adjusted based on the information from the filter clogging monitoring apparatus 61.

The bed-side system 6 is mainly constructed of the filter clogging monitoring apparatus 61 having a display apparatus that displays a status of clogging of a filter 621 for blood purification, and a blood purification apparatus 62 that performs blood purification processing based on the information from the filter clogging monitoring apparatus 61, adjusts the amount of medicine administered to the patient and controls the flow rate of the blood.

The filter clogging monitoring apparatus 61 is mainly constructed of a pressure measurement section 612 that measures pressures in the filter 621, a calculation section 611 that analyzes pressure waveforms obtained from pressure differences calculated in consideration of pressure information from the pressure measurement section 612, and when necessary, other information (blood hematocrit value, blood viscosity information, protein concentration information and osmotic information) and that detects a status of clogging, a memory 613 that stores various kinds of information used in analysis of the clogging of the filter, a display section 615 that displays the status of the filter clogging and the various kinds of information used in the calculation, and flow rate control section and medicine dosage amount control section 623 of the blood purification apparatus based on the status of filter clogging calculated in the calculation section 611.

The blood purification apparatus 62 is mainly constructed of the filter 621, a blood inflow portion-side drip-chamber 626 provided upstream of the filter 621, a blood outflow portion-side drip-chamber 627 provided downstream of the filter 621, a rotary pump 625 provided on a circulation path 632 of blood upstream of the blood inflow portion-side drip-chamber 626, a flow rate control section 622 that controls flow rates of rotary pumps 630 and 629 that adjust the flow rate of waste liquid provided respectively for tubes 628 and 631 attached to a coupler of the filter 621 and the blood flow rate of the rotary pump 625 provided on the circulation path 632 based on the information from the filter clogging monitoring apparatus 61, a medicine dosage section 624 that doses medicine such as an anti-coagulant into the circulation path 632, and a medicine dosage amount control section 623 that controls the amount of medicine dosed into the circulation path 632 based on the information from the filter clogging monitoring apparatus 61.

The operation of the bed-side system with the above-described configuration will be described below.

The blood circulates from a patient 63 to the patient 63 along the circulation path 632 through the filter 621 mounted on the blood purification apparatus 62. In the blood purification apparatus 62, a pressure Pa at the blood inflow portion-side drip-chamber 626, pressure Pv at the blood outflow portion-side drip-chamber 627, pressure Pf1 at the coupler on the blood inflow portion side of the filter 621, and pressure Pf2 at the coupler on the blood outflow portion side of the filter 621 are measured by the pressure measurement section 612 in the filter clogging monitoring apparatus 61. Herein, the pressure Pa at the blood inflow portion-side drip-chamber 626 corresponds to the pressure in the blood inflow portion of the filter, the pressure Pv at the blood outflow portion-side drip-chamber 627 corresponds to the pressure in the blood outflow portion of the filter, the pressure Pf1 at the coupler on the blood inflow portion side of the filter 621 corresponds to the pressure in the filtrate inflow portion of the filter, and the pressure Pf2 at the coupler on the blood outflow portion side of the filter 621 corresponds to the pressure in the filtrate outflow portion of the filter.

These pressures are output from the pressure measurement section 612 to the calculation section 611. The calculation section 611 calculates pressure differences based on the pressure information from the pressure measurement section 612, and when necessary, information from a continuous hematoclit monitor 64, viscosity information from the outside, protein concentration information, osmotic information, and flow rate information from the blood purification apparatus 62, analyzes the waveforms, and detects a status of the filter clogging based on the analysis results.

The status of the filter clogging obtained in the calculation section 611 is output to the control section 614. The control section 614 controls the flow rate control section 622 and the medicine dosage amount control section 623 of the blood purification apparatus 62. The flow rate control section 622 controls the flow rate of the blood that circulates inside the circulation path 632 based on the status of filter clogging. For example, the section 622 sets an optimal blood flow rate based on a table that associates a filter clogging status with a blood flow rate, and outputs the flow rate information to the rotary pump 625. The rotary pump 625 adjusts the flow rate of the blood based on the flow rate information from the flow rate control section 622.

Further, the flow rate control section 622 controls the flow rate of waste liquid that passes through the tubes 628 and 631 of the filter 621 based on the filter clogging status. For example, the section 622 sets an optimal waste liquid flow rate based on a table that associates a filter clogging status with a waste liquid flow rate, and outputs the flow rate information to the rotary pumps 630 and 629. The rotary pumps 630 and 629 adjust the flow rate of waste liquid based on the flow rate information from the flow rate control section 622. At this point, the flow rate control section 622 may control the rotary pumps 630 and 629 similarly or individually corresponding to the clogging status of the filter 621.

The medicine dosage amount control section 623 controls the amount of medicine to be dosed into the circulation path 632 based on the filter clogging status. For example, the section 623 sets an optimal amount of medicine dosage based on a table that associates filter clogging information with an amount of medicine dosage, and outputs the medicine dosage amount information to the medicine dosage section 624. The medicine dosage section 624 adjusts a dosage amount of medicine based on the medicine dosage amount information from the medicine dosage amount control section 623, and doses the adjusted dosage amount of medicine into the circulation path 632.

More specifically, when the vertical clogging of the filter deteriorates, the medicine dosage amount control section 623 makes a setting so as to increase the dosage amount of an anti-coagulant, and controls the medicine dosage section 624 to dose the set dosage amount of the anti-coagulant into the circulation path 632. Further, the flow rate control section 622 makes a setting so as to increase the blood flow rate, and controls the rotary pump 625 to circulate the blood at the set flow rate. It is thereby possible to prevent the filter clogging from developing and extend the time until the filter is clogged. Further, it is possible to prevent a blood loss due to the fact such that the blood remains inside the filter (residual blood) when the blood in the circuit is returned to the patient to finish the blood purification, and that the blood in the circuit cannot be returned to the patient (inability to recover blood) because of drastic clogging.

When the lateral filter clogging deteriorates, the medicine dosage amount control section 623 makes a setting so as to increase the dosage amount of an anti-coagulant, and controls the medicine dosage section 624 to does the set amount of the anti-coagulant into the circulation path 632. Further, the flow rate control section 622 makes a setting so as to decrease the flow rate of waste liquid, and controls the rotary pumps 630 and 629 to filter the waste liquid at the set flow rate. It is thereby possible to reduce the filtering capability per unit time and extend the time until the filter is clogged. In addition, a case where control is performed to reduce the flow rate of waste liquid is explained, but it may be possible to perform control to increase the flow rate of waste liquid corresponding to the situation.

Thus, the bed-side system according to this embodiment enables detection, display and monitoring of a status of filter clogging, etc., according to this embodiment at the bed side in real-time. Further, in the bed-side system, it is possible to store information collected or analyzed at the bed side and use the information to adjust the flow rate of blood or waste liquid or the amount of medicine dosage, etc.

The configurations of the bed-side system and the filter monitoring apparatus are not limited to the configurations as shown in FIG. 18. That is, the present invention is capable of being carried out into practice with various modifications of the apparatuses within the scope where it is possible to analyze pressure waveforms based on the collected pressure information, obtain a status of filter clogging, and perform control of blood purification based on the information.

Thus, according to the method in this embodiment, since it is possible to recognize a status of filter clogging with higher precision, the clogging is detected early, and it is thereby possible to adjust a dosage amount of the anti-coagulant properly without overdosage, vary the setting of the flow rate of blood, and prevent the clogging of the filter from developing. It is also possible to predict the time during which blood purification can be executed (completion timing), which allows medical staff to prepare for completing blood purification with a sufficient time. Further, it is possible to prevent a blood loss of a patient caused by the blood remaining in the filter (residual blood) at the end of blood purification. Furthermore, the risk is reduced that blood cells are suctioned by a strong negative pressure, and destruction of blood cells (hemolysis, etc.) develops. Moreover, it is possible to set more effective operating conditions considering the reduction in substance removal capability (clearance) due to filter clogging.

Further, it is possible to evaluate how clogging occurs in each filter, and use the evaluation results for the development of a filter in which clogging hardly occurs.

As described above, according to the present invention, by continuously measuring at least one pressure selected from the group consisting of a pressure in the blood inflow portion, a pressure in the blood outflow portion, a filtering pressure in the blood inflow portion, and a filtering pressure in the blood outflow portion and analyzing the variations with time, a status of filter clogging is detected and recognized with higher precision, for example, the clogging is detected early, and it is thereby possible to prevent the filter clogging from developing by adjusting a dosage amount of the anti-coagulant properly without overdosage and varying the setting of the flow rate of blood.

This application is based on the Japanese Patent Application No 2003-041731 filed on Feb. 19, 2003, entire content of which is expressly incorporated by reference herein.

The invention claimed is:

1. A method for detecting filter clogging comprising:
   flowing blood through a hollow-fiber membrane from a blood inflow portion to a blood outflow portion, a waste liquid from the blood passing through the hollow filter membrane into a filtrate region;
   flowing a filtrate into the filtrate region through a filtrate inflow portion and out of a filtrate outflow portion;
   measuring pressure over time in at least two of the blood inflow portion, the blood outflow portion, the filtrate inflow portion, and the filtrate outflow portion and generating measured pressure signals indicative thereof;
   analyzing the measured pressure signals including determining a transform of the measured pressure signals and a difference of a phase in the transformed measured pressure signals indicative of measured pressure in at least two of the blood inflow portion, the blood outflow portion, the filtrate inflow portion, and the filtrate outflow portion;
   in response to determining a difference in the phase that is indicative of clogging of the hollow-fiber membrane, at least one of display filter clogging status and adjusting an amount of anti-coagulant in the blood entering the blood inflow portion.

2. The method according to claim 1, wherein the analyzing step further includes determining a Fast Fourier Transform of the measured pressure signals.

3. The method according to claim 2, wherein the Fast Fourier Transform corresponds to a pulsing frequently in at least one of the blood inflow portion and the filtrate outflow portion.

4. The method according to claim 1, wherein the analyzing steps includes:
   transforming the measured pressures to generate a transform value; and
   determining an amplitude and/or a power of the transformed transformed measured pressure signals.

5. The method according to claim 4, wherein the analysis step further includes:
   determining a ratio of amplitude and/or power in at least two of the blood inflow portion, the blood outflow portion, the filtrate inflow portion, and the filtrate outflow portion.

6. An apparatus for monitoring a filter clogging comprising:
   pressure sensors for detecting pressures in at least two of a blood inflow portion, a blood outflow portion, a filtrate inflow portion, and a filtrate outflow portion of a blood dialysis filter, and generating pressure signals indicative thereof;
   a calculation section which analyzes the detected pressures by transforming the measured pressures, determining phase of the pressure signals, determining changes in the phase of the pressure signals, and a clogging status of the filter based on changes in the phase;
   a display for displaying the filter clogging status determined by the calculation section; and
   a medical dosage section, the calculation section controls the medical dossage section to adjust an amount of anti-coagulant introduced in blood pumped to the blood inflow portion in accordance with the clogging status.

7. A bed-side system comprising the apparatus according to claim 6.

8. The apparatus according to claim 6, wherein the calculation section determines the changes in the phases of the pressure signals indicative of pressures measured in at least two of the blood inflow portion, the blood outflow portion, the filtrate inflow portion, and the filtrate outflow portion.

9. The apparatus according to claim 6, wherein the calculation section further determines a frequency transform of the pressure signals and calculates the changes in the phases based on the frequency transform of the pressure signals.

10. A bedside blood filter apparatus comprising:
a blood filter including a blood inflow portion, a blood outflow portion, and a hollow-fiber membrane disposed between the blood inflow portion and the blood outflow portion, waste products from the blood passing through the hollow fiber membrane;
a filtrate inflow portion for receiving a liquid filtrate and a filtrate outflow portion through which the filtrate and the waste products are discharged;
a plurality of pressure sensors disposed in at least one of the blood inflow portion, the blood outflow portion, the filtrate inflow portion, and the filtrate outflow portion;
a pump for pumping blood to the blood inflow portion;
a calculation section which calculates a clogging status of the hollow-fiber filter, the calculation section including a processor programmed to determine changes in phase of the measured pressure and determining the clogging status in accordance with the determined phase changes;
a medical dosage section, the calculation section controls the medication dosage section to adjust an amount of anticoagulant introduced into blood pumped to the blood inflow portion in accordance with the determined clogging status.

11. The blood filtering apparatus according to claim 10, wherein the calculation section processor is further programmed to determine a difference in phase of pressures measured in at least two of the blood inflow portion, the blood outflow portion, the filtrate inflow portion, and the filtrate outflow portion.

12. The blood filtering apparatus according to claim 11, wherein the calculation section processor is further programmed to generate a frequency transform on the measured pressures and determine the phase difference based on transforms of the measured pressures.

13. The blood filtering apparatus according to claim 12, wherein the frequency transform includes a Fourier transform.

* * * * *